US011678842B2

(12) United States Patent
Lynch et al.

(10) Patent No.: US 11,678,842 B2
(45) Date of Patent: Jun. 20, 2023

(54) SENSING STRATEGIES FOR HEALTH ASSESSMENT OF OSSEOINTEGRATED PROSTHESES

(71) Applicant: THE REGENTS OF THE UNIVERSITY OF MICHIGAN, Ann Arbor, MI (US)

(72) Inventors: Jerome P. Lynch, Ann Arbor, MI (US); Wentao Wang, Ann Arbor, MI (US)

(73) Assignee: THE REGENTS OF THE UNIVERSITY OF MICHIGAN, Ann Arbor, MI (US)

(*) Notice: Subject to any disclaimer, the term of this patent is extended or adjusted under 35 U.S.C. 154(b) by 309 days.

(21) Appl. No.: 16/642,122

(22) PCT Filed: Aug. 30, 2018

(86) PCT No.: PCT/US2018/048926
§ 371 (c)(1),
(2) Date: Feb. 26, 2020

(87) PCT Pub. No.: WO2019/139644
PCT Pub. Date: Jul. 18, 2019

(65) Prior Publication Data
US 2020/0352505 A1 Nov. 12, 2020

Related U.S. Application Data

(60) Provisional application No. 62/552,599, filed on Aug. 31, 2017.

(51) Int. Cl.
*A61B 5/00* (2006.01)
*A61F 2/76* (2006.01)
(Continued)

(52) U.S. Cl.
CPC .......... *A61B 5/4851* (2013.01); *A61B 5/4504* (2013.01); *A61B 5/6811* (2013.01);
(Continued)

(58) Field of Classification Search
CPC ... A61B 5/4504; A61B 5/4851; A61B 5/6811; A61F 2/76; A61F 2002/30784
See application file for complete search history.

(56) References Cited

U.S. PATENT DOCUMENTS 3,947,897 A * 4/1976 Owens ...................... A61F 2/80
                                                        623/57
5,330,481 A 7/1994 Hood et al.
(Continued)

FOREIGN PATENT DOCUMENTS

WO  WO-2000-28925 A2    5/2000
WO    WO-0028925 A2 *   5/2000  ......... A61F 2/30771
WO  WO-2017120484 A1    7/2017

OTHER PUBLICATIONS

Wang, Wentao et al. "Ultrasonic longitudinal waves to monitor the integration of titanium rods with host bone." Proceedings of Spie vol. 10168. Apr. 12, 2017.
(Continued)

*Primary Examiner* — Christie L Bahena
(74) *Attorney, Agent, or Firm* — Harness, Dickey & Pierce, P.L.C.

(57) ABSTRACT

A method and an osseointegrated prosthesis system having an osseointegrated prosthesis member are provided having a monitoring system operably coupled to the osseointegrated prosthesis member configured to quantitatively assess the osseointegration of the osseointegrated prosthesis member, a wave-generating element coupled to the osseointegrated prosthesis member and configured to output guided waves along the osseointegrated prosthesis member interrogating an interface between bone and the osseointegrated prosthesis
(Continued)

member, and a sensing system configured to sense a condition of the interface between bone and the prosthesis.

15 Claims, 16 Drawing Sheets

(51) Int. Cl.
    *A61F 2/30*     (2006.01)
    *A61F 2/60*     (2006.01)
    *A61F 2/78*     (2006.01)

(52) U.S. Cl.
    CPC ...... *A61F 2/76* (2013.01); *A61F 2002/30784* (2013.01); *A61F 2002/608* (2013.01); *A61F 2002/7887* (2013.01); *A61F 2310/00023* (2013.01)

(56) References Cited

U.S. PATENT DOCUMENTS

| | | | |
|---|---|---|---|
| 5,730,705 | A | 3/1998 | Talish et al. |
| 7,097,662 | B2 | 8/2006 | Evans, III et al. |
| 9,579,222 | B2 | 2/2017 | Branemark et al. |
| 2008/0243216 | A1 | 10/2008 | Zilberman et al. |
| 2009/0131838 | A1 | 5/2009 | Fotiadis et al. |
| 2012/0190989 | A1 | 7/2012 | Kaiser et al. |
| 2014/0156022 | A1 | 6/2014 | Holt et al. |
| 2016/0354216 | A1 | 12/2016 | Hugate |

OTHER PUBLICATIONS

Wang, Wentao et al. "Numerical and experimental simulation of linear shear piezoelectric phased arrays for structural health monitoring." Proceedings of Spie vol. 1016. Apr. 19, 2017.

Extended European Search Report issued in European Application No. 18899857.9 dated Apr. 30, 2021.

International Search Report and Written Opinion of the ISA issued in PCT/US2018/048926, dated Aug. 9, 2019; ISA/KR.

Gupta S, Loh KJ. Noncontact Electrical Permittivity Mapping and pH-Sensitive Films for Osseointegrated Prosthesis and Infection Monitoring. IEEE Trans Med Imaging. Nov. 2017;36(11):2193-2203. doi: 10.1109/TMI.2017.2707390. Epub May 23, 2017. PMID: 28541895.

A. Rowlands, F.A. Duck, J.L. Cunningham, "Bone vibration measurement using ultrasound: Application to detection of hip prosthesis loosening", Medical Engineering & Physics, vol. 30, Issue 3, 2008, pp. 278-284.

"A Smart Prosthetic Knee with In-Vivo Diagnoses" News Mediacom 2014.

Wang, W. and Lynch, J. P., (2018). "Application of Guided Wave Methods to Quantitatively Assess Healing in Osseointegrated Prostheses," Journal of Structural Health Monitoring, Sage, accepted and in press. Jul. 2, 2018.

Wang, W., and Lynch, J. P. (2018). "Identification of Bone Fracture in Osseointegrated Prostheses using Rayleigh Wave Methods," Proceedings of SPIE: Smart Structures and Materials, Denver, CO. Mar. 27, 2018.

Wang, W. and Lynch, J.P. (2017) "Guided Wave Analysis of Osseointegration at Bone-Prosthesis Interfaces," Proceedings of the 11th International Workshop on Structural Health Monitoring, Stanford, CA. Sep. 2017.

\* cited by examiner

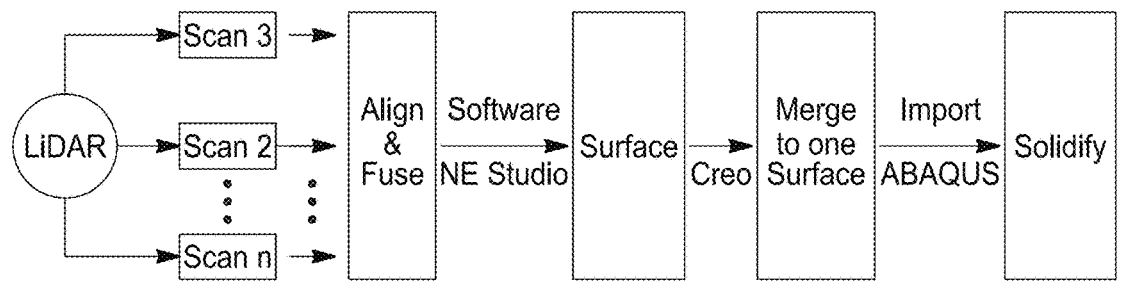
*Fig-4A*
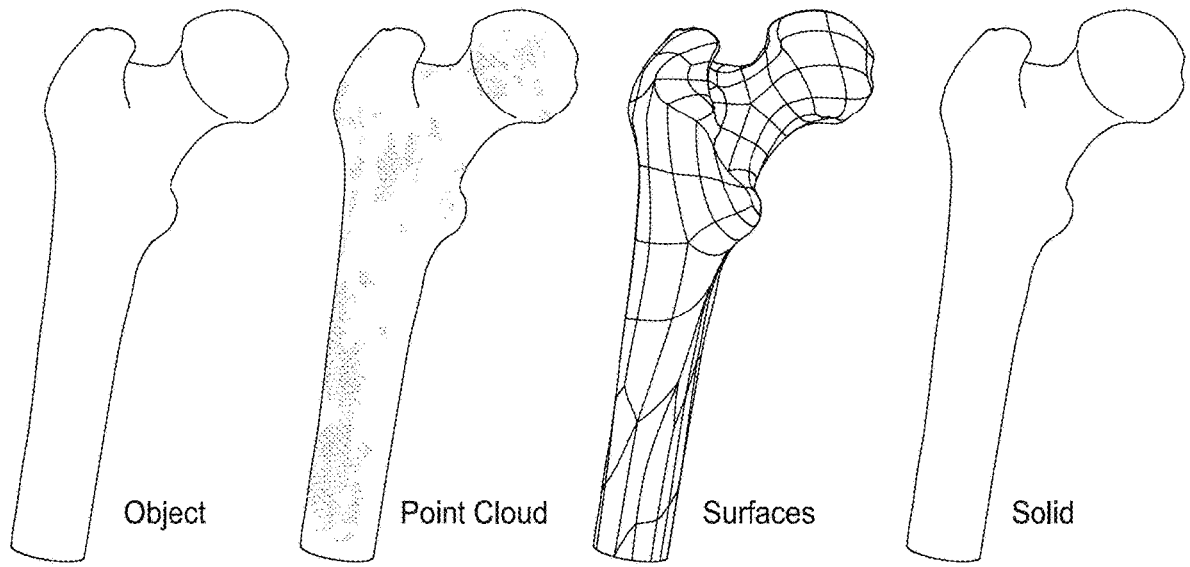
Object | Point Cloud | Surfaces | Solid
*Fig-4B*
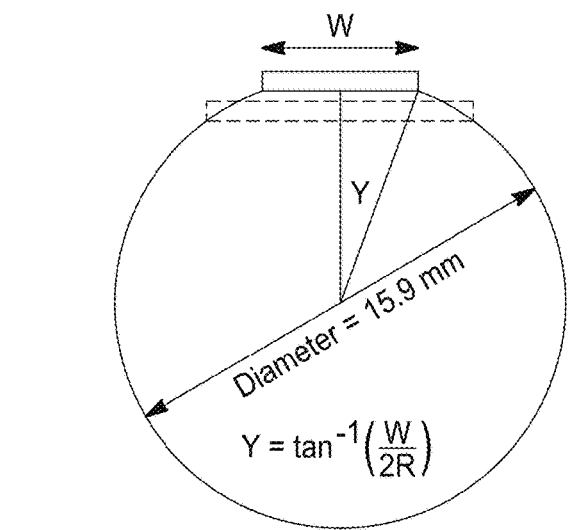
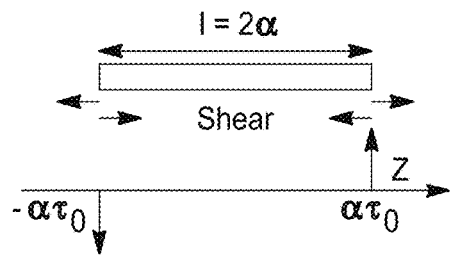
*Fig-5A*

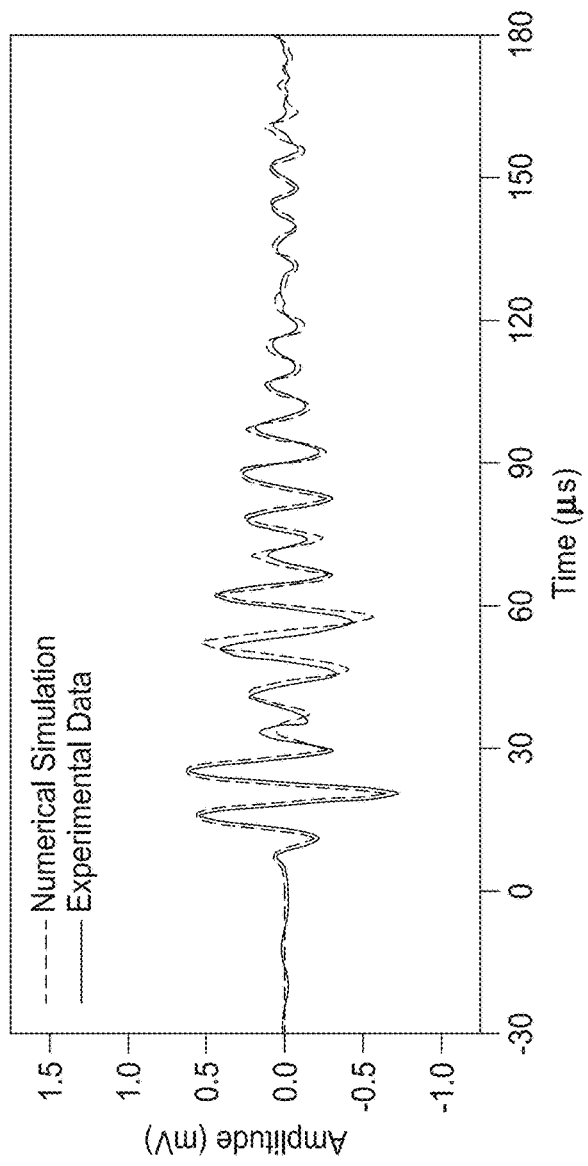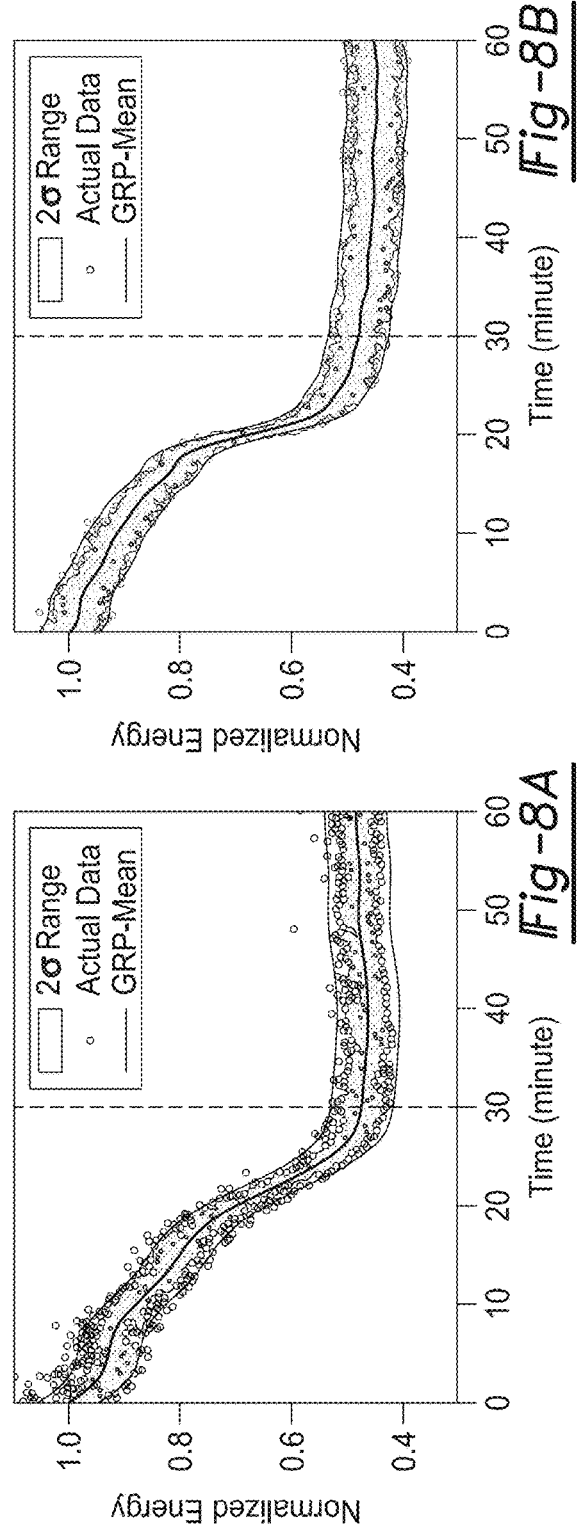

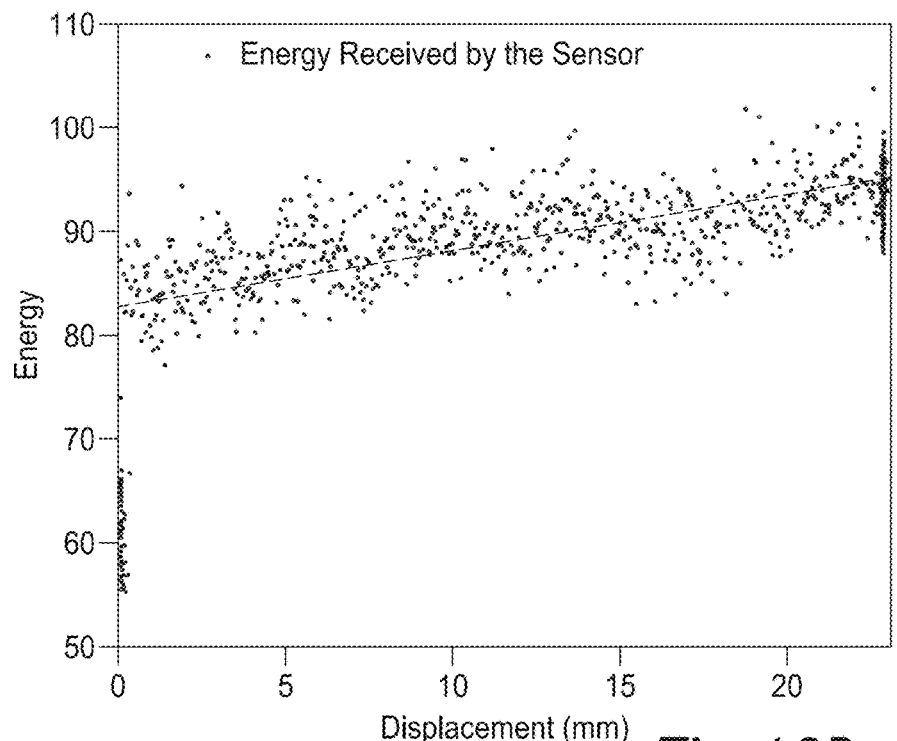
Fig-10D
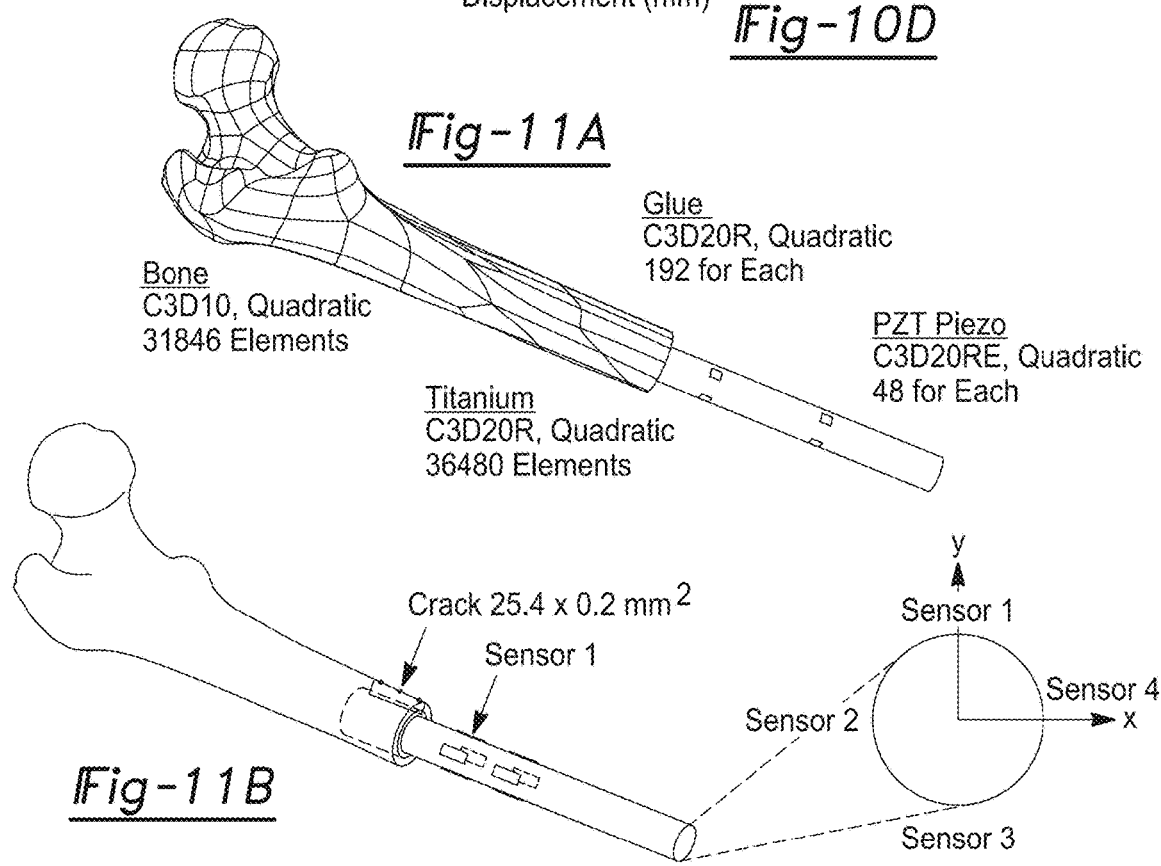
Fig-11A
Fig-11B

SENSING STRATEGIES FOR HEALTH ASSESSMENT OF OSSEOINTEGRATED PROSTHESES

CROSS-REFERENCE TO RELATED APPLICATIONS

This application is the U.S. National Phase Application under 35 U.S.C. 371 of International Application No. PCT/US2018/048926, filed Aug. 30, 2018, which claims the benefit of U.S. Provisional Application No. 62/552,599, filed on Aug. 31, 2017. The entire disclosures of the above applications are incorporated herein by reference.

GOVERNMENT INTEREST

This invention was made with government support under N00014-16-1-2738, awarded by the U.S. Navy, Office of Naval Research. The Government has certain rights in the invention.

FIELD

The present disclosure relates to sensing strategies for health assessment of osseointegrated prostheses.

BACKGROUND AND SUMMARY

This section provides background information related to the present disclosure which is not necessarily prior art. This section provides a general summary of the disclosure, and is not a comprehensive disclosure of its full scope or all of its features.

Traumatic limb loss affects approximately 2 million individuals in the United States. Prosthetic limbs offer an improvement in the quality of life of amputees. The dominant prosthesis design today is the socket prosthesis which consists of a socket that attaches to the residual arm or leg with the artificial limb (and joint) attached to the socket body. While tremendous advances have been made in the comfort and performance of socket prostheses, some drawbacks remain. Specifically, socket prostheses can be uncomfortable under continued use, the fit of the prosthesis can change with time, and the skin of the residual limb can experience chaffing and the development of soars at the socket surface 2. Also, socket prostheses may not be an option for extremely short residual limbs and when the residual limb is severely wounded and deformed (as can be the case with veterans who have lost a limb due to an explosive device). Further areas of applicability will become apparent from the description provided herein.

An alternative prosthetic solution is osseointegrated prostheses which are surgically implanted into the bone of the residual limb. The prosthesis consists of a structural anchor that is surgically inserted into the bone of the limb with the prosthesis exposed through the skin and an artificial limb is attached to a protruding taper adapter (FIG. 1). Three osseointegrated prosthesis designs exist in the market including: screw-shaped titanium prostheses (e.g., OPRA marketed by Integrum), press-fit chrome cobalt molybdenum alloy or titanium prostheses (e.g., those marketed by Eska/OrthoDynamics/Permedica), and compression titanium prostheses (e.g., marketed by Zimmer-Biomet). The OPRA and press-fit devices are the most common osseointegrated designs and consist of solid rod fixtures that are surgically implanted into the host bone. While osseointegrated prostheses eliminate many of the drawbacks of socket prostheses, they have their own limitations. First, there is a lack of quantitative methods that can ascertain when an osseointegrated prosthesis can be loaded. Rehabilitation protocols that govern when an osseointegrated prosthesis can be loaded is based on doctor judgement. Additional limitations include: 1) long term risk exposure of tissue and bone to infections due to biofilms entering the limb via the prosthesis, and 2) bone fracture during the life of the prosthesis. There is a growing need to monitor the integration and long-term performance of osseointegrated prostheses in order to accurately identify when a prosthesis can be loaded Monitoring can also help to identify issues such as loosening of the prosthesis fixture and fracture in the host bone overtime. Currently, clinical evaluation of osseointegration is based on X-ray imaging. The method is qualitative due to doctor interpretation of X-ray images; patients are also exposed to radiation. In addition, X-ray techniques cannot be used to measure the bone-interface because of diffraction effects due to the presence of titanium.

Structural health monitoring (SHM) technologies have the potential to offer doctors a quantitative approach to monitoring osseointegrated prostheses including assessment of bone healing post-surgery and damage to the bone during long-term prosthesis use. Of specific interest is assessment of the bone-prosthesis interface where osseointegration occurs because this interface is where load transfer occurs from the prosthesis to the skeletal system. While sensors could be explored for implantation in the body, such a strategy would be challenged by issues such as biocompatibility of the sensor, the cost of sensor placement, and the long-term survivability of the sensor itself. An alternative strategy is to adopt sensors that reside outside of the body thereby eliminating biocompatibility concerns and lessening the regulatory review process. Guided wave methods are an ideal candidate because sensors can be installed outside the body but the prosthesis can be leveraged as a wave guide where guided waves can interrogate the bone-prosthesis interface. The SHM research community has only recently begun to explore SHM strategies for the monitoring of healing in orthopedic systems.

According to the principles of the present teachings, a guided wave strategy is provided to quantitatively assess the osseointegration of osseointegrated prostheses over their complete life-span using wearable monitoring systems. To generate guided waves in the prosthesis, piezoelectric wafers, among other wave-generating elements, are provided for installation within or on the surface of the osseointegrated prosthesis (such as, but not limited to, the percutaneous end of the osseointegrated prosthesis). In some embodiments, the present teachings focus on the use of the energy content of the guide waves introduced in the prosthesis using an array of $d_{31}$-type piezoelectric wafers installed on the prosthesis circumference to track osseointegration at the bone-prosthesis interface or other bone or impact conditions. During osseointegration, the bone grows into the porous surface of the prosthesis with bone density and elastic modulus simultaneously increasing; these changes result in increased energy absorption of the guided waves. In some embodiments, the present teachings explore the use of the energy content of the fundamental longitudinal wave mode to assess cases of loosening and pullout of the prosthesis that can be associated with bone infections and fractures. To enhance the accuracy of the guided wave method, the present teachings provide a method of optimizing the sizing of the piezoelectric wafers used to excite the longitudinal wave mode in a solid cylindrical prosthesis fixture using the theory of guided waves. The present disclosure verifies the efficacy of the guided wave method to assess osseointegration using both numerical simulation and experimental validation methods. A synthetic femur bone with a titanium rod serving as the prosthesis fixture is adopted for numerical and experimental modeling.

The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure. Corresponding reference numerals indicate corresponding parts throughout the several views of the drawings.

FIG. 4A is a 3D laser scanning process of a femur according to the principles of the present teachings.

FIG. 4B is the progression of the actual femur object into a solid model for analysis.

FIG. 5A is a schematic of the piezoelectric wafer dimensions and the simplified pin-force model.

FIG. 7B shows after fully osseointegration (100%).

FIG. 8A shows GPR results of signal energy vs. epoxy solidified time of sample 1.

FIG. 8B shows GPR results of signal energy vs. epoxy solidified time of sample 2.

FIG. 10D is sample 2 stage 2 of pull-out experimental results.

FIG. 11A is a numerical model in ABAQUS of a meshed titanium prosthesis implanted into sawbone bone.

FIG. 11B is a schematic of the crack and sensor locations of a numerical model in ABAQUS.

DETAILED DESCRIPTION

Figure 1:
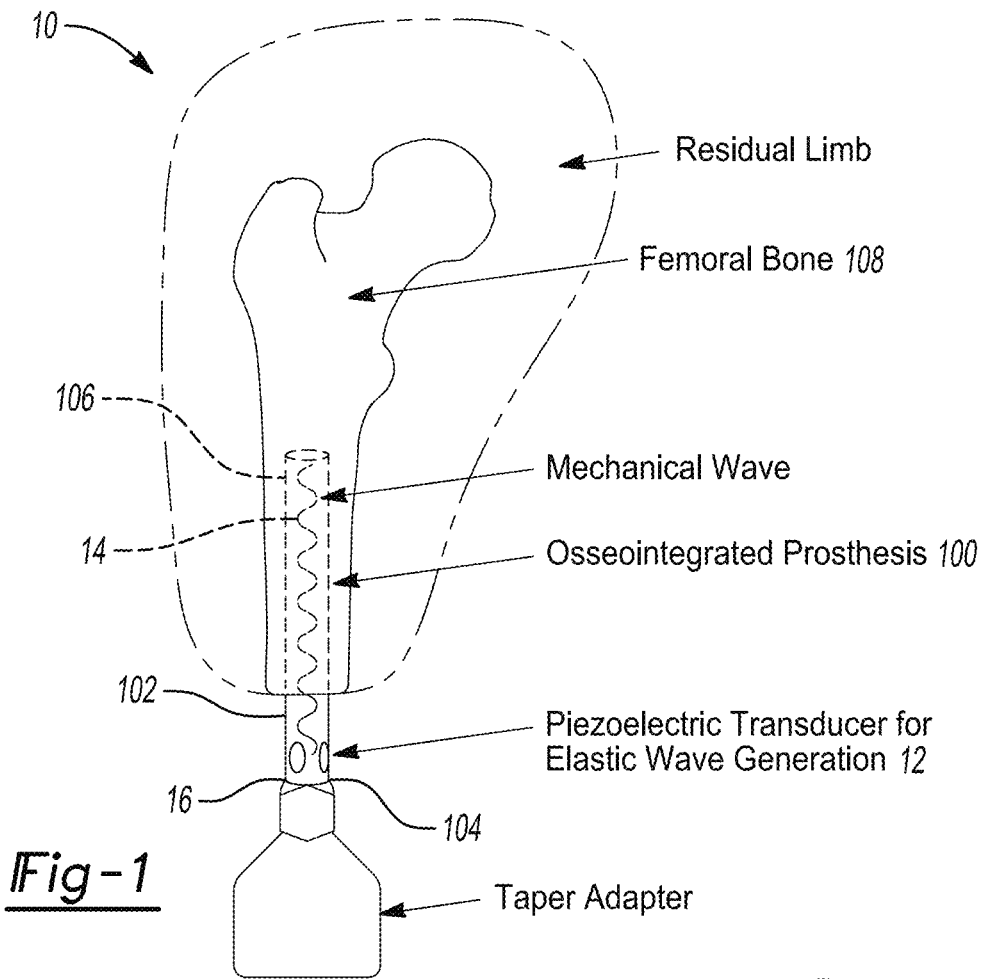
FIG. 1 is a sensing architecture of osseointegrated prostheses using guided waves according to the principles of the present teachings.

Example embodiments will now be described more fully with reference to the accompanying drawings. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

According to the principles of the present teachings, an apparatus 10 and method are provided to monitor the healing and long-term performance of osseointegrated prostheses 100 comprising one or more wave-generating elements 12, such as but not limited to piezoelectric wafer elements, lasers, contact elements, non-contact elements, and the like, bonded or otherwise operably coupled and/or associated to the surface 102 of the prosthesis 100 (FIG. 1), such as on a percutaneous end 104. The elastic stress waves 14 generated in the prosthesis fixture will propagate along the longitudinal axis of the prosthesis 100. The strategy of exploiting the prosthesis 100 as a wave guide is attractive because it effectively allows sensors 16 outside of the human body to interrogate the properties of the bone-prosthesis interface 106 where osseointegration will occur after placement of the prosthesis 100. It also provides a method of tracking the long-term performance of the interface 106 to detect issues, such as, but not limited to, loosening of the prosthesis 100 attributed to bone infection and fracture of the host bone 108. In the present disclosure, a solid titanium rod with a radial dimension equivalent to the OPRA and press-fit prostheses is adopted for the study of guided wave methods for monitoring osseointegration in femoral bones. However, it should be understood that the principles of the present teachings are not limited to the particular prosthesis described, but are equally applicable to other prosthesis, such as, but not limited to, any structure that touches or contacts bones.

Figure 2A:
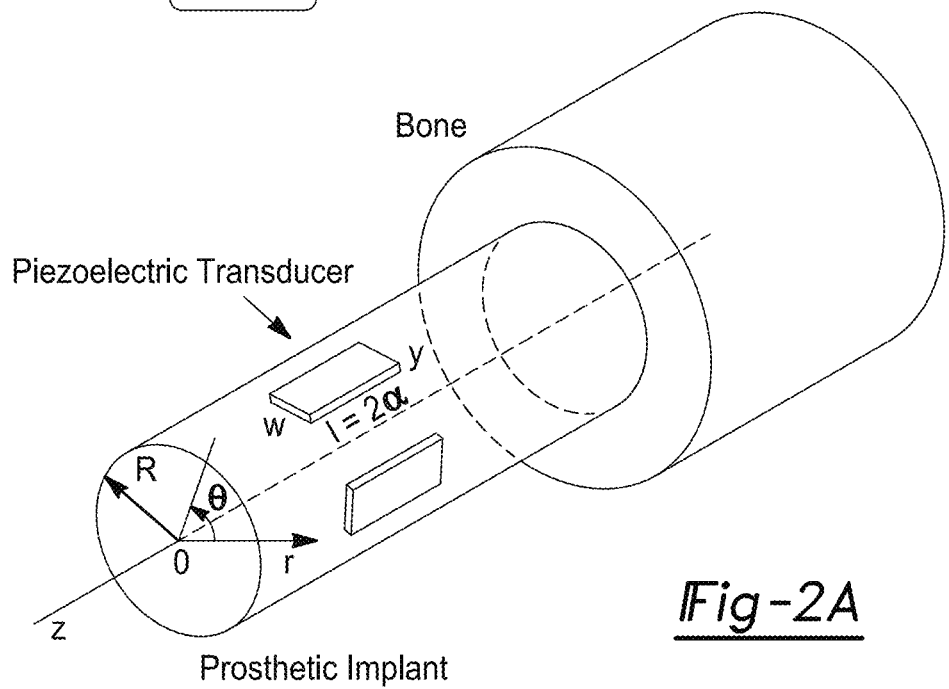
FIG. 2A is a schematic of the prosthesis-bone model coordinate system according to the principles of the present teachings.

Consider now an elastic, isotropic solid rod defined in cylindrical coordinates (where r, z and θ are the radial, longitudinal, and angular coordinates, respectively) as shown in FIG. 2A. Waves in an elastic isotropic body with no body forces applied can be analytically expressed by Navier equations in cylindrical coordinates. Navier equations are often simplified to describe displacements in a body, u, as a sum of a dilational scalar potential, Φ, and an equivoluminal vector potential field, H. In the case of a solid rod, the boundary at the rod surface (r=R) is assumed to be traction-free where the state of stress is stated as $\sigma_{rr}=\sigma_{r\theta}=\sigma_{rz}=0$. Fundamentally, the scalar potential field Φ and vector potential field H satisfy the following wave equations:

$$\frac{\partial^2 \Phi}{\partial r^2} + \frac{1}{r}\frac{\partial \Phi}{\partial r} + \frac{1}{r^2}\frac{\partial^2 \Phi}{\partial \theta^2} + \frac{\partial^2 \Phi}{\partial z^2} = \frac{1}{c_P^2}\frac{\partial^2 \Phi}{\partial t^2} \quad (1)$$

$$\left(\nabla^2 H_r - \frac{H_r}{r^2} - \frac{2}{r^2}\frac{\partial H_\theta}{\partial \theta}\right)\vec{e}_r + \\ \left(\nabla^2 H_\theta - \frac{H_\theta}{r^2} + \frac{2}{r^2}\frac{\partial H_r}{\partial \theta}\right)\vec{e}_\theta + \nabla^2 H_z \vec{e}_z = \frac{1}{c_S^2}\frac{\partial^2 H}{\partial t^2} \quad (2)$$

where $\nabla^2$ is the 3-dimensional Laplace operator, $c_p=\sqrt{\lambda+2\mu/\rho}$ and $c_s=\sqrt{\mu/\rho}$ are the pressure and shear wave velocities in the medium (which are 6070 m/s and 3310 m/s for titanium, respectively), t is time, ρ is the material density, μ is the material shear modulus, λ is the material Lamé constant, $H_r$, $H_\theta$, and $H_z$ are the components of vector potential function H in cylindrical coordinates, and $\vec{e}_r$, $\vec{e}_\theta$, and $\vec{e}_z$ are the unit basis vectors that define the cylindrical coordinate system itself.

The components of the scalar and vector fields in equations (1) and (2) for harmonic waves are of the form:

$$\Phi = f \cdot \cos n\theta \, \cos(\omega t + \xi z) = AJ_n(\alpha r)\cos n\theta \, \cos(\omega t + \xi z) \quad (3)$$

$$H_r = h_r \cdot \sin n\theta \, \sin(\omega t + \xi z) = BJ_{n+1}(\beta r)\sin n\theta \, \sin(\omega t + \xi z) \quad (4)$$

$$H_\theta = h_\theta \cdot \cos n\theta \, \sin(\omega t + \xi z) = -BJ_{n+1}(\beta r)\cos n\theta \, \sin(\omega t + \xi z) \quad (5)$$

$$H_z = h_z \cdot \sin n\theta \, \cos(\omega t + \xi z) = CJ_n(\beta r)\sin n\theta \, \cos(\omega t + \xi z) \quad (6)$$

where $$\alpha^2 = \frac{\omega^2}{c_P^2} - \xi^2, \, \beta^2 = \frac{\omega^2}{c_S^2} - \xi^2,$$

n is the wave order (which is an integer value of zero or greater), $J_n$ are Bessel's functions of the first kind, ξ is the wavenumber, ω is the angular frequency, and A, B, and C are constants. Substituting the components stated in equations (3) to (6) into equations (1) and (2), the displacement field can be stated:

$$u_r = \left[\frac{df}{dr} + \frac{n}{r}h_z + \xi h_r\right]\cos n\theta \cos(\omega t + \xi z) \quad (7)$$

$$u_\theta = \left[-\frac{n}{r}f + \xi h_r - \frac{dh_z}{dr}\right]\sin n\theta \cos(\omega t + \xi z) \quad (8)$$

$$u_z = \left[-\xi f - \frac{dh_r}{dr} - \frac{n+1}{r}h_r\right]\cos n\theta \sin(\omega t + \xi z) \quad (9)$$

Figure 2B:
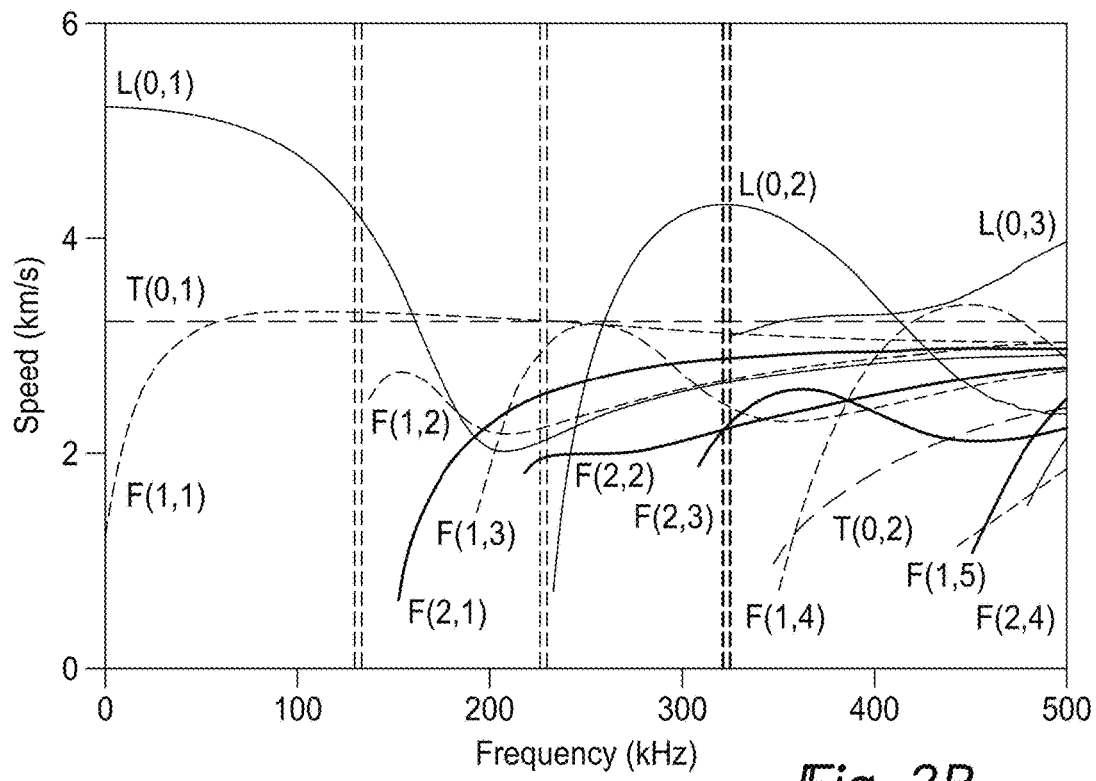
FIG. 2B shows group velocity curves for guided waves in titanium rod with a 15.9 mm diameter.

The general displacement field in the rod can be decomposed into three harmonic wave modes: longitudinal modes, L(0,m), which exist when $u_\theta$ vanishes; torsional modes, T(0,m), which exist when $u_r$ and $u_z$ both vanish; and flexural modes, F(n,m), which consist of all three displacement components, where the mode order is defined by n and the mode number is defined by integer values of m. The longitudinal and torsional modes are axially symmetric while the flexural modes are non-axisymmetric. The generation of different guided wave modes depends on the piezoelectric element type used, spatial configuration of the piezoelectric element, and the nature of the excitation signal. Guided waves in a rod exhibit dispersion (except for the lowest order torsional mode) which means the propagation velocity of the mode varies with the excitation frequency. In this study, a prosthetic fixture implanted in bone will be a titanium rod with a 15.9 mm diameter. The material properties for titanium considered herein are: elastic modulus (E) of 110 GPa, density ($\rho$) of 4330 kg/m$^3$, and Poisson's ratio (v) of 0.30). FIG. 2B presents the theoretical group velocities of the various wave modes in a 15.9 mm diameter titanium. The vertical lines in the figure are cutoff frequencies representing the point where higher order modes are generated for each of the three mode types. The generation of these different wave modes are based on the piezoelectric element type used (e.g., $d_{31}$ versus $d_{36}$ piezoelectric), spatial configuration of the actuators, and the nature of the excitation signal (e.g., frequency content). FIG. 13 depicts the three primary modes in a 15.9 mm diameter titanium rod (solid) along with the dispersion curve corresponding to phase velocity.

A synthetic bone model is adopted to explore how osseointegration at the bone-prosthesis interface affects the fundamental longitudinal wave mode in a prosthesis fixture. A synthetic femur bone is acquired from Sawbones Worldwide (Model 3406-5) to serve as a host to a titanium rod serving as a prosthesis fixture. The femoral sawbone is manufactured from a solid rigid polyurethane foam material (with a density of 1600 kg/m$^3$). Sawbones are a popular alternative to human cadaver bone for biomechanics research given the degree of mechanical realism the synthetic bone provides. To ensure realism in the experimental study, the density of the synthetic sawbone was selected to ensure the bone has an acoustic impedance (5.66×10$^6$ kg/m$^2$ s) similar to that of human femoral bones (6×10$^6$ kg/m$^2$ s). The bone is cut in half to have a length of 25 cm and its interior is reamed to provide a snug fit for a 15.9 mm diameter titanium rod implanted to a depth of 2.54 cm.

Figure 3A:
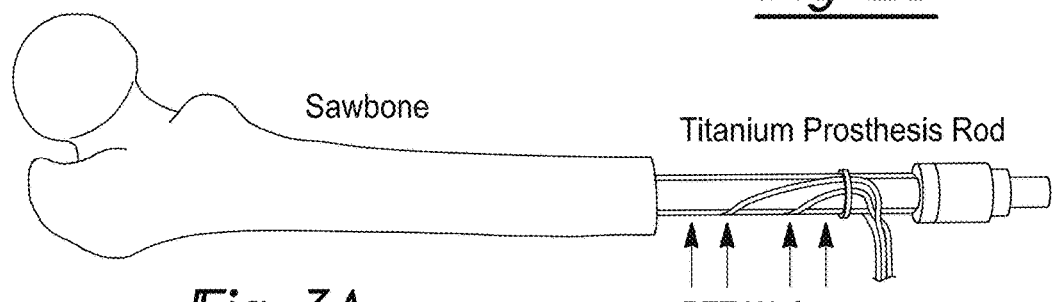
FIG. 3A is a perspective view of a femur sawbone with titanium prosthesis rod of an osseointegrated prosthesis-bone model.
Figure 3B:
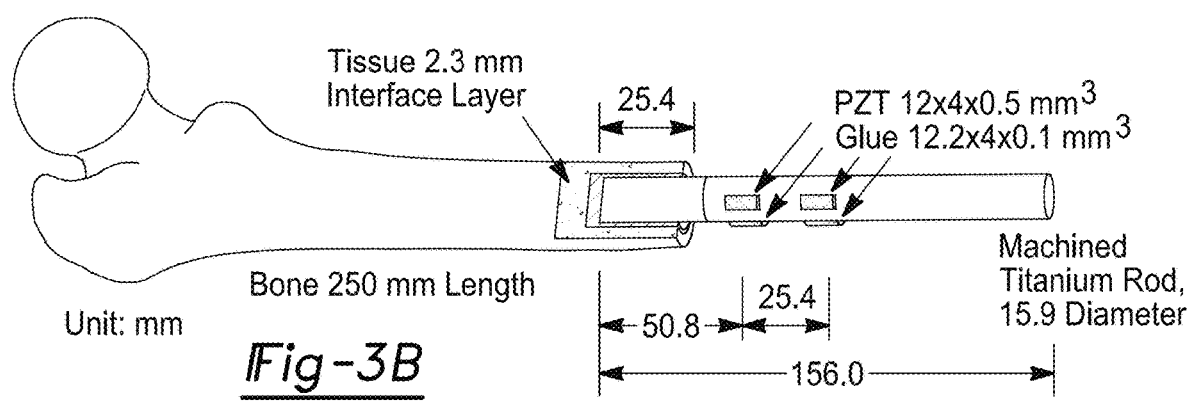
FIG. 3B is a perspective view of a titanium rod in host bone model of an osseointegrated prosthesis-bone model.

A solid isotropic (Grade 5) titanium rod with a diameter of 15.9 mm and length of 15.60 cm is selected as the prosthesis fixture and machined to allow 8 PZT wafers (Piezo Systems PSI-5A4E) to be attached. The PZT wafers are 0.508 mm thick and cut from larger wafers to be 12 mm long and 4 mm wide (sizing of the wafers will be discussed later). Piezoelectric sensors are placed on the side (e.g., circumferential side) of the rod instead of at its end because the end of the prosthesis will have a complex joint with an artificial limb attached. Placement on the side also allows for potential replacement of the PZT wafers with time and offers opportunity to generate different wave modes (longitudinal, torsional, and flexural modes) in the prosthesis. The rod is machined to provide perfectly flat surfaces 12.2 mm long and 4 mm wide at the quarter points of the rod circumference at two circumference locations. In some embodiments, the two circumferential arrays are centered 76.2 mm and 50.8 mm from the rod's percutaneous end. The PZT wafers are bonded to the rod surface using standard cyanoacrylate glue. The rod with PZT elements bonded can be implanted into the sawbone to the full machined depth (2.54 cm) as shown in FIGS. 3A and 3B. To excite the longitudinal wave mode in the rod, the first array of PZT elements is excited with a three cycle tone-burst waveform whose center frequency is 100 kHz. By exciting all four elements of the PZT array, only the longitudinal wave mode will be generated. The second array of PZT elements will be used to measure the time history of the longitudinal wave propagating along the length of the prosthesis fixture.

In order to introduce the desired fundamental wave into the titanium rod, a three-cycle Hanning window tone-burst signal is employed as the excitation signal:

$$V(t) = A_w[H(t) - H(t - N_c/f_c)]\left(1 - \cos\frac{2\pi f_c t}{N_c}\right)\sin(2\pi f_c t) \quad (10)$$

where $A_w$ is the wave amplitude, H(t) is the Heaviside function, and $N_c$=3 and $f_c$ are the cycle numbers and the center frequency of the excitation signal, respectively. The center frequency is selected to ensure higher order modes are not introduced (see the dispersion curve of FIG. 2B) and to maximize the strain field based on the size of the PZT element (as will be discussed later). However, it should be understood that the principles of the present teachings are not limited to the particular waveform described (Equation 10), but are equally applicable to any other waveform that is either finite in duration or infinite.

A finite element model is first created to numerically simulate the waves generated in the prosthesis and the mechanical interaction between the bone and the prosthesis fixture during wave propagation in the prosthesis. The finite element (FE) modeling platform ABAQUS (Dassault Systemes) is adopted to model the femur sawbone-titanium rod osseointegration model.

To accurately model the complex three-dimensional (3D) geometry of the femur, laser scanning and photogrammetry is utilized to acquire a precise digital mapping of the femur surface geometry (FIG. 4). The NextEngine 3D scanner is used to capture the femur sawbone surface using lasers generating 3D point clouds and cameras mapping RGB values to the surface topology points. Using an automated turn table, a full 360° scan of the femur was conducted. The turning table rotates to 10 positions (poses) and 4 laser beams are used to scan the surface topology at each pose. The laser scanner provides a comprehensive point cloud with a density of 150 sample points per inch. NextEngine Studio is used to align the point clouds generated by the various poses to generate 1635 curved surfaces that constitute the complete femur. The curved surfaces are then merged to form one complete solid model using Creo 4.0. The meshed solid model of the femur is then imported to ABAQUS for analysis.

The ABAQUS model (FIG. 3B) is divided into five geometric parts: bone, titanium rod, PZT element, bone tissue at the prosthesis surface, and bond layer between the PZT and prosthesis. The use of numerical platforms such as ABAQUS (or any other finite element method package) to model wave mechanics requires an appropriate selection of mesh size and time increment. Both are highly dependent on the frequency and wavelength of the wave modes. First, the time step size must be sufficient to accurately capture the propagating waveform with enough samples to unambiguously represent the waves. In effect, this means the sampling frequency must exceed, at a minimum, two times the highest wave frequency of interest but standard practice is to sample five or more times the highest frequency of interest. Second, the element size (spatial domain) must be small enough to accurately capture the wavelength of the wave field. In general, the element size must be a small fraction of the smallest wavelengths anticipated.

The titanium rod is isotropic and modeled with mechanical properties as follows: elastic modulus $E_{tit}$=110 GPa, density $\rho_{tit}$=4330 kg/m$^3$, and Poisson's ratio $v_{tit}$=0.30. The rod is meshed using C3D20R (20-node, quadratic brick) solid elements. For the guided wave in the rod, using a 100-kHz excitation signal, the wavelengths of the first longitudinal, torsional, and flexural modes are calculated as $\lambda_L$=47.64 mm, $\lambda_T$=32.3 mm and $\lambda_F$=33.1 mm, respectively. The feature size of the solid element is selected to be 1 mm resulting in more than 30 nodes per wavelength and a total of 36,480 elements for the titanium rod.

The femur bone is meshed using a 10-node, quadratic tetrahedron element (C3D10) with a feature size of 4 mm resulting in a total of 31,846 solid elements. The density of the bone is 2000 kg/m$^3$. The anisotropic material properties in Table 1 are used for the femur bone properties with orientation defined in the cylindrical coordinate system. It is noted that the values in Table 1 are modified values of density, elastic modulus and Poisson's ratio of the bone based on model updating using experimental results. A cavity is created in ABAQUS to define the interior surface of the femur. A varying element size strategy is taken for the femur bone to reduce computational cost.

TABLE 1

Material properties of the femur*

| Young's Modulus (GPa) | Shear Modulus (GPa) | Poisson's ratios |
|---|---|---|
| $E_1$ = 16.0 | $G_{12}$ = 3.3 | $v_{12}$ = 0.30 |
| $E_2$ = 6.8 | $G_{23}$ = 3.6 | $v_{12}$ = 0.45 |
| $E_3$ = 6.8 | $G_{13}$ = 3.3 | $v_{12}$ = 0.30 |

*1-direction is longitudinal to femur main axis; 2- and 3-directions are orthogonal to longitudinal axis The 20-node, quadratic piezoelectric brick elements (C3D20RE) are used for the PZT elements with 12×4 mm$^2$ in area and 0.504 mm thickness. The density of PZT is 7500 kg/m$^3$. The piezoelectric properties are obtained from the piezoelectric manufacturer (Piezo Systems) and imported in ABAQUS format (Tables 2 and 3). The grid in length and width is 1 mm with 4 elements in the thickness direction for the PZT wafer, which results in 192 elements per PZT element. The bottom surface (at the rod surface) of each PZT element is grounded with 0 electric potential, and the top surface is excited by a surface charge related to the excitation signal.

TABLE 2

Elastic stiffness constants, $C_{ij}^E(10^{10}$ N/m$^2)$, for PZT

| Material | $C_{11}^E$ | $C_{12}^E$ | $C_{13}^E$ | $C_{33}^E$ | $C_{44}^E$ | $C_{66}^E$ |
|---|---|---|---|---|---|---|
| PSI-5A4E | 15.2 | 10.2 | 10.0 | 12.7 | 2.1 | 2.5 |

TABLE 3

Piezoelectric coefficients, $d_{ij}(10^{-12}$ C/N$^2)$, and dielectric constants, $\varepsilon_{ij}(10^{-8}$ F/m), for PZT

| Material | $d_{31}$ | $d_{33}$ | $d_{15}$ | $\varepsilon_{11}$ | $\varepsilon_{22}$ | $\varepsilon_{33}$ |
|---|---|---|---|---|---|---|
| PSI-5A4E | −191 | 430 | 590 | 1576 | 1576 | 1727 |

The bond layer is a 0.1 mm thickness cyanoacrylate glue between the PZT and prosthesis. The size of the bond layer is 12.2×4×0.1 mm$^3$ with the density of 1250 kg/m$^3$ and the elastic modulus of 3.5 GPa. C3D20R (20-node, quadratic brick) solid elements are used to mesh the bond layer. Constraint type "Tie" is created between the PZT bottom surface (master surface) and the bond layer's top surface (slave surface). Similarly, another tie constraint pair is created between the bond bottom layer (master surface) and the surface of the titanium rod (slave surface) to transfer the force from the PZT element to the surface of the prosthesis.

A total of 6095 quadratic tetrahedron elements (C3D10) are employed to model interfacial bone tissue existing between the prosthetic implant and the femoral bone. The material properties of this layer are based on femur bone properties, while all are set as variables to simulate osseointegration. The bone surface tissue is selected to be a 2.3 mm layer tied to both the titanium rod and the bone's cylinder cavity as constraints. The thickness of this connective bone layer is based on the minimum bone cover needed for OPRA implants (2 mm). The constraint pairs are the titanium to tissue's internal surface (master to slave surface pair, respectively) and the tissue's outer surface to bone's internal cavity (master to slave surface pair, respectively).

Three-cycle tone burst signals with center frequencies of 100 kHz are applied simultaneously to the four PZT actuators on the same circumference. The time step in the ABAQUS/Implicit is chosen as 0.2 μs. The numerical model has been validated and updated based on experimental result, which will be presented in the next section.

To monitor osseointegration occurring at a bone-prosthesis interface, guided waves are generated at the percutanous end of the prosthesis fixture, in some embodiments. These waves radiate along the longitudinal axis (z) of the prosthesis and reflect at the fixture ends. The guided waves will interact with bone and soft tissue at the surface of the rod resulting in an absorption of wave energy. The measured energy in the wave signal as a function of time will be directly dependent of the interface between the solid prosthesis and the bone. Hence, changes in the bone-prosthesis interface such as bone attachment and growth into the porous surface of the prosthesis osseointegration) will increase the absorbed wave energy at the interface. In this study, the energy content of guided wave modes is considered as a quantitative basis, in addition to others described herein, of assessing the mechanical properties of the prosthesis-bone interface.

Ideally, the wave mode introduced in the prosthesis wave guide should be easy to excite with piezoelectric wafer elements mounted on the fixture surface. Furthermore, it should have a high signal-to-noise ratio (SNR) for accurate wave acquisition using piezoelectric wafer elements mounted on the fixture surface. The fundamental longitudinal mode (L(0,1)) selectively excited in the low frequency spectrum (lower than the cutoff frequency for the second flexural mode) is provided because at low frequencies the fundamental longitudinal mode dominates, thereby simplifying the wave field and reducing coherent noise from higher modes. While flexural and torsional modes can exist at these lower frequency bands (as shown in the dispersion curve of a titanium rod in FIG. 2B), the piezoelectric actuation strategy will ensure longitudinal modes are selectively generated. To generate the fundamental longitudinal wave field, a $d_{31}$-type piezoelectric wafer array (made from lead zirconate titanate (PZT) ceramic wafers) is installed on the circumference (i.e., circumferential side) of the prosthesis rod with all elements of the array excited by the same electrical signal. However, it is well understood that other methods are available to generate and sense guided waves besides PZT elements, including non-contact methods such as lasers. Each piezoelectric element is defined by length, l, width, w, and thickness y. Four elements are mounted to the quarter points of the circumference of the prosthesis fixture to serve as actuator and sensor arrays that generate and sense the longitudinal wave, respectively. The piezoelectric wafer dimensions and signal frequency must be optimized to ensure guided wave modes have large strain fields; this ensures a high SNR for the waves measured in the prosthesis.

The compatibility established between a piezoelectric wafer and host structure is achieved through interfacial shear stress $\tau(z, t)$. In the case of ideal bonding (no shear lag across the piezoelectric wafer-structure interface), the shear stress induced in the structure can be modeled using the simplified pin-force model where the shear exists only at the wafer boundaries. Thus, the shear stress along the longitudinal axis that is induced by the piezoelectric wafer, $\tau(z, t)$, in harmonic excitation can be expressed as:

$$\tau(z,t) = a\tau_0[\delta(z-a) - \delta(z+a)]e^{i\omega t} \quad (11)$$

where a is the half-length of the piezoelectric wafer, $a\tau_0$ is the pin force magnitude applied at the end of the piezoelectric wafer, $\delta(\cdot)$ is Dirac function in space (in this case, applied at the ends of the 2a long wafer), $\omega$ is the excitation frequency, and t is time. Here, the harmonic component is generalized to $e^{i\omega t}$ but later, only the real component of the solution will be of interest.

The principles of the present disclosure tunes the piezoelectric size to maximize the amplitudes of the strain fields associated with the fundamental longitudinal wave in a solid titanium rod with a 15.9 mm diameter. To simplify the analysis, it is performed in the wavenumber ($\xi$) domain by applying the Fourier transform to functions defined in the space (z) domain:

$$\tilde{g}(\xi) = \int_{-\infty}^{\infty} g(z) e^{-i\xi z} dz \quad (12)$$

The expressions for the scalar and vector fields (equations (1) and (2)), the assumed form of the field components (equations (3) to (6)), the displacement fields (equations (7) to (9)) and stress fields can be transformed to the wavenumber domain using equation (12). However, a new boundary condition is applied to reflect the harmonic wave generation at the piezoelectric surface where r=R. Specifically, for the fundamental longitudinal mode (n=0) the boundary conditions in the wavenumber domain at the piezoelectric wafer can be specified as:

$$\tilde{\sigma}_{rr}|_{r=R} = \tilde{\sigma}_{r\theta}|_{r=R} = 0$$

$$\tilde{\sigma}_{rz}|_{r=R} = \tilde{\tau}_a = (-2i \sin \xi a) a\tau_0 e^{i\omega t} \quad (13)$$

where $\tilde{\sigma}_{rz}|_{r=R}$ is essentially the pin-force shear model transformed to the wavenumber domain.

As illustrated herein, the solution for the z-component of the wave field displacement, as defined in the wavenumber domain, is:

$$\tilde{u}_z = \frac{\partial \tilde{\Phi}}{\partial z} + \frac{1}{r}\frac{\partial}{\partial \theta}(r\tilde{H}_\theta) - \frac{1}{r}\frac{\partial \tilde{H}_r}{\partial \theta} \quad (14)$$

where $\tilde{\Phi}$, $\tilde{H}_r$, $\tilde{H}_\theta$, and $\tilde{H}_z$ are the components of the scalar and vector fields in equations (3) to (6) in the wavenumber domain via the Fourier transform (equation (12)). The displacement in the physical domain could be obtained by applying the residue theorem in the evaluation of the integral of the inverse Fourier transform via the sum of residues $$u_z(z, \theta, t)|_{r=R} = \quad (15)$$
$$2a\tau_0 \left( \sum_{\xi^L} i\xi^L \frac{L_A(\xi^L)}{D_0(\xi^L)} J_0(\alpha R) - \sum_{\xi^L} \frac{L_B(\xi^L)}{D_0(\xi^L)} \beta J_0(\beta R) \right)$$
$$\sin \xi^L a \, e^{i(\xi^L z - \omega t)}$$

Here $L_A$, $L_B$, and $D_0$ are functions that depend on the excitation signal frequency and piezoelectric wafer dimensions as shown herein.

In summary, equation (15) indicates the guided wave modes can be tuned in the rod via $\sin \xi^L a$. The maximum displacement magnitude occurs when $\xi^L a = (2n-1)\pi/2$ resulting in $\sin \xi^L a = 1$; consequently, a wave mode will not be excited when $\xi^L a = n\pi$. The guided wave mode tuning principles derived here for an active piezoelectric transducer apply equally well for a receiver (sensing) piezoelectric transducer. Thus, the amplitude of the induced wave mode will change with both the central frequency of the excitation signal that induces the wavelengths of the wave field and the length of the piezoelectric wafer.

The 15.9 mm diameter titanium rod is now considered with rectangular PZT piezoelectric transducers bounded to the rod circumference. The PZT wafers are assumed to be 0.508 mm thick based on the piezoelectric wafers used later during experimental validation (hence, y=0.508 mm). The rod is machined to offer a perfectly flat rectangular surface prior to bonding. This approach to preparing the rod for the piezoelectric wafers will control the width, w, of the wafer. To machine no deeper than 5% of the radius, R, the wafer width, w, is selected to satisfy the function $\gamma = \tan^{-1}(w/2R) < 18.2°$ (see FIG. 5A). Hence, for the 15.9 mm diameter rod, this results in a maximum width of 4.95 mm. In this study, the width is selected to be w=4 mm.

Figure 5B:
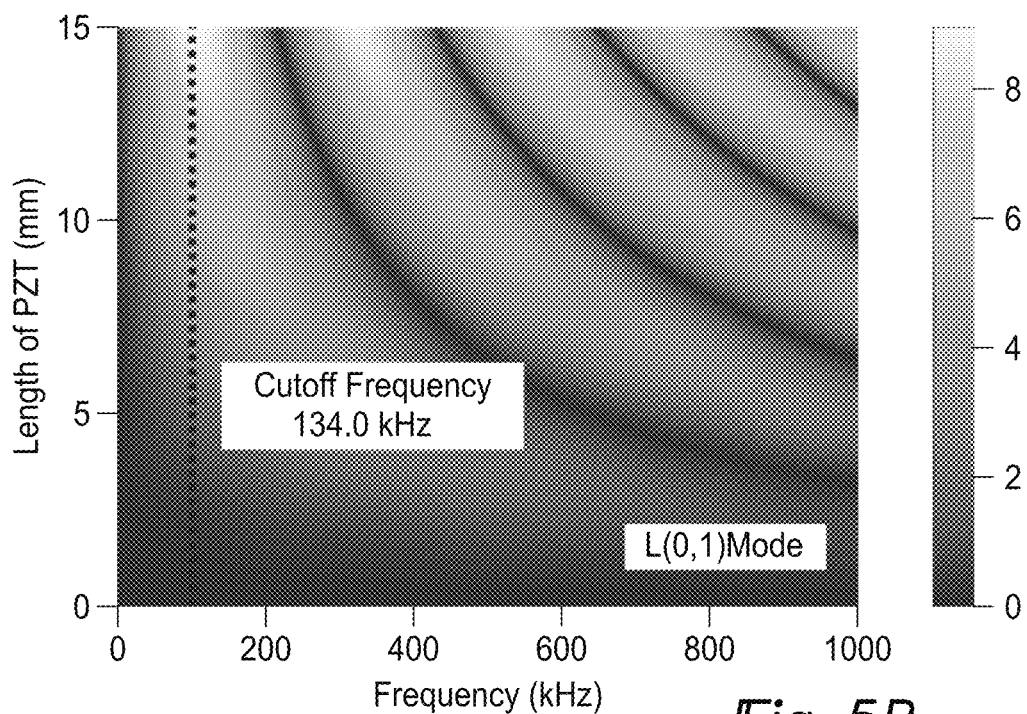
FIG. 5B is a tuning curve (sin $\xi^L a$) of the L(0,1) mode.

The tuning process to maximize the longitudinal wave field displacement described previously is used to select the wafer length, l. FIG. 5B plots the absolute value of $\sin \xi^L a$ as a function of wave frequency and element wafer length, l=2a, to allow an appropriate length wafer to be selected. The relationship between the longitudinal wave wavenumber, $\xi$, and frequency, $\omega$ is simply $\omega^L = \xi^L c_{ph}^L$, where $c_{ph}^L$ is the phase velocity of the longitudinal mode.

Figure 5C:
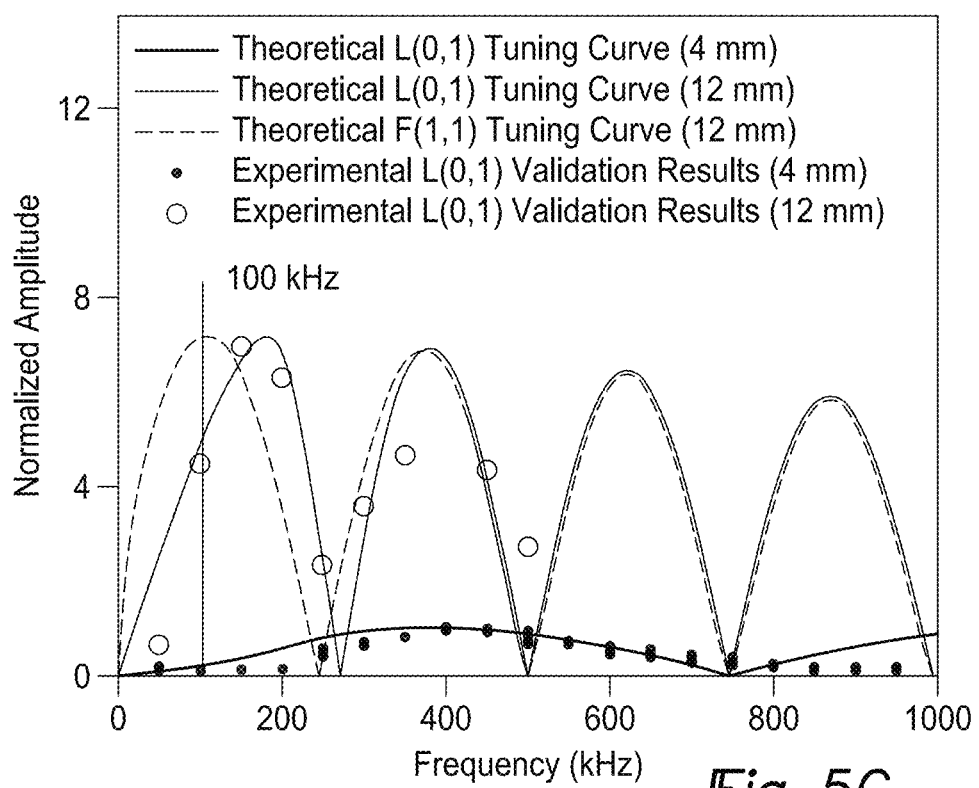
FIG. 5C shows validated tuning curves.

Two lengths of wafer are considered here: 4 mm and 12 mm. Considering FIG. 5B, the normalized maximum surface displacement (equation (15)) is plotted for each wafer size considered in FIG. 5C. While the previous tuning procedure considered only the fundamental longitudinal mode, similar tuning equations for the first flexural mode can also be derived (as for any other guided wave mode). The same tuning curves are plotted in FIG. 5C for the flexural modes. There is a stark difference in the normalized amplitudes between 12 mm and 4 mm with the 12 mm long wafer offering a much larger amplitude for both the first longitudinal and flexural modes; hence, 12 mm wafers will be elected in this study.

Next, the excitation frequency of the PZT wafer is considered. For the 15.9 mm diameter titanium rod, the cutoff frequencies of the flexural, longitudinal and torsional modes are 134.0 kHz, 231.6 kHz, and 345.6 kHz, respectively. To suppress higher order wave modes, the excitation frequency should be set to below 134.0 kHz. Based on the tuning curve of FIG. 5C, an excitation frequency of 100 kHz is selected because it provides nearly equal benefit to the longitudinal and flexural modes.

A key element of the numerical model is the ability to assess changes in the longitudinal mode energy content as osseointegration occurs. A model of osseointegration associated with healing bone is established based on experimental data provided by Manjubala et al. Their study provides a detailed model of adult bone properties during healing including increases in bone density (p) and elastic modulus (E). Their study also reveals the random nature of bone changes over a surface as healing occurs.

To investigate the effects of interfacial tissue on the acoustic impedance signature of the longitudinal wave mode in the prosthesis, the spatial distribution of changes in the bone elastic modulus and density is simulated by a macro scripted in Python for ABAQUS. The script randomly selects elements to form 10 groups with elements in each group to have specific elastic modulus and density values. The average elastic modulus and density of the bone tissue is ranged from 1 kPa and 1 kg/m$^3$ (approximately 0% healing) to 16.0 GPa and 2000 kg/m$^3$ (i.e., 100% of the bone modulus and density under mature osseointegration), with increments of 3.2 GPa and 400 kg/m$^3$ (i.e., 20%). The elastic modulus and density of each group is defined as the average elastic modulus and density multiplied by a scaling factor. The scaling factor ranges from 0.98 to 1.02 with a unique scaling factor assigned to each group. A full osseointegration is defined as when the average elastic modulus and density of the bone surface tissue reach the mature femur bone properties in Table 1. Thus, the degree of osseointegration of each stage is on average 0%, 20%, 40%, 60%, 80% and 100%±2%.

Figure 6A:
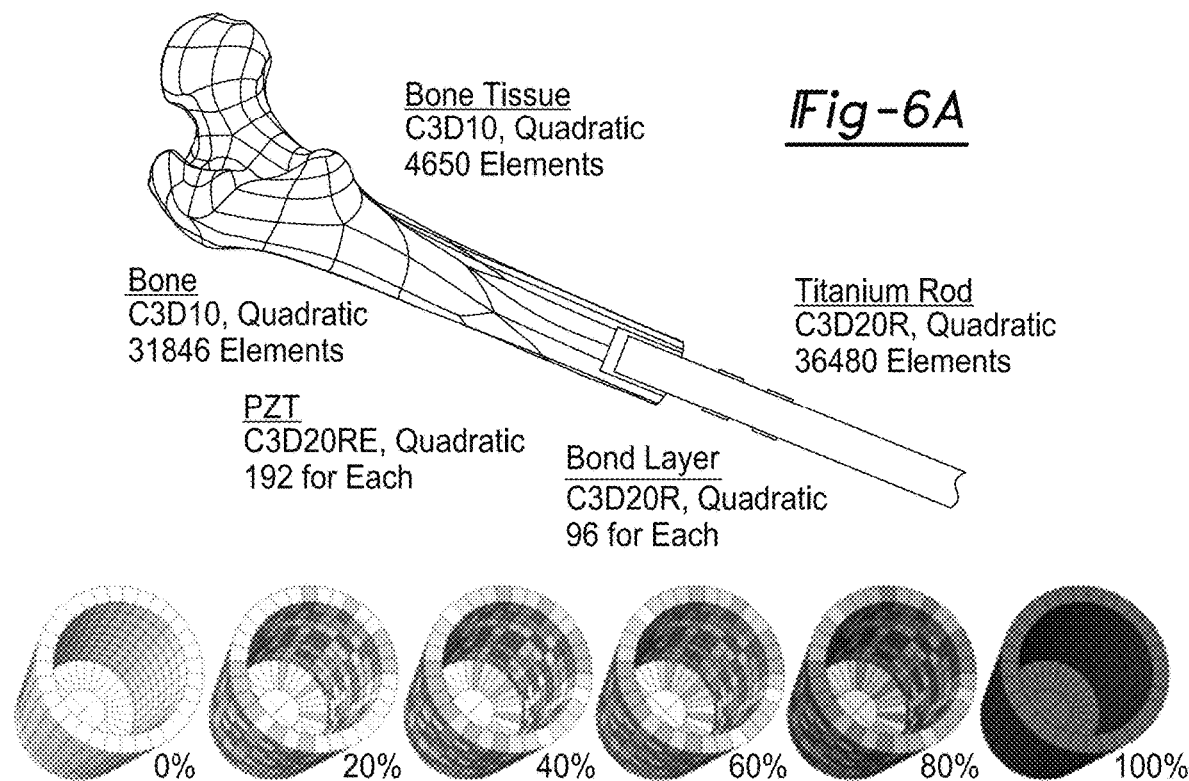
FIG. 6A is a numerical model and osseointegrated bone tissue.
Figure 6B:
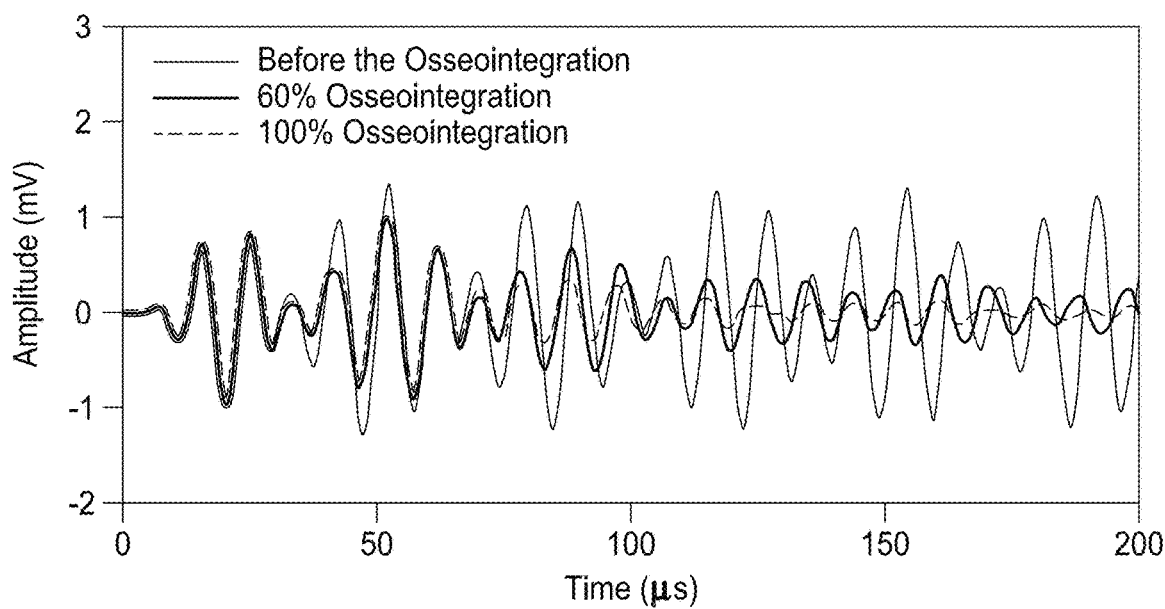
FIG. 6B shows waveforms received by the sensor on the titanium rod.
Figure 6C:
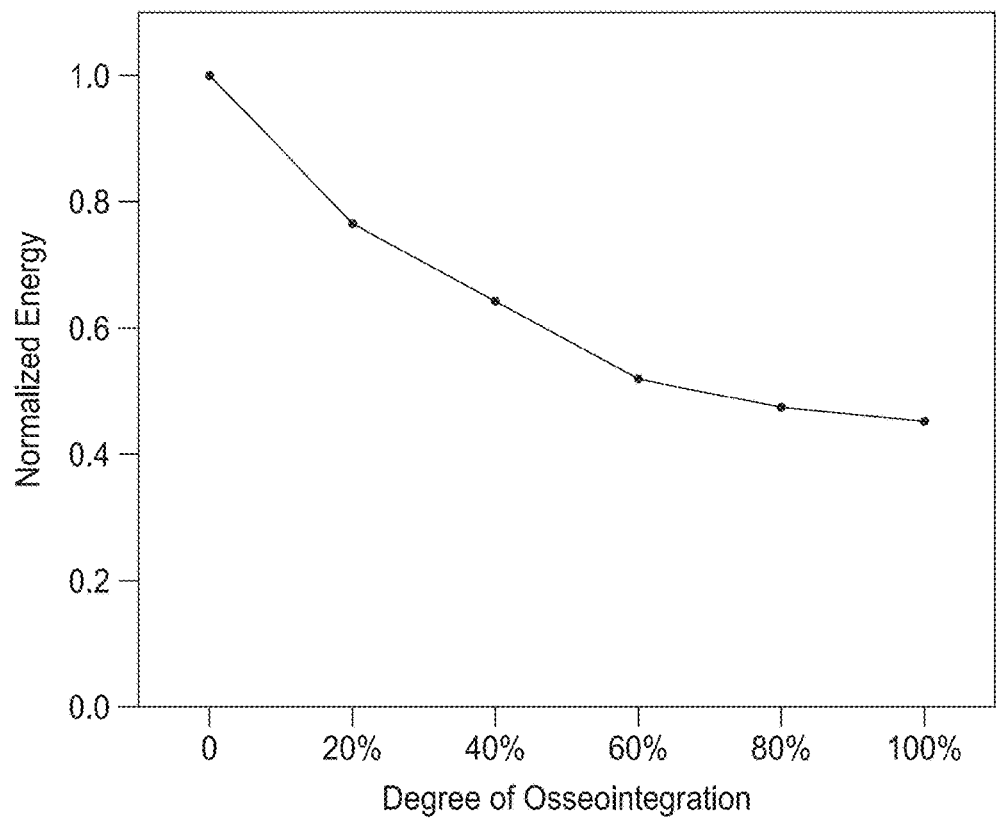
FIG. 6C is the energy of waveform with various degree of osseointegration.

The osseointegrated model is simulated by ABAQUS/Implicit. The fundamental longitudinal mode (L(0,1)) of guided waves propagating in the titanium rod (FIG. 6A) is received by the sensor array and transferred to the electric potential waveform as shown in FIG. 6B). The energy of the waveform $E_s$ is calculated according to $$E_s = \Sigma_{i=1}^{N} |s_i|^2 \quad (16)$$

where, $s_i$ is the amplitude of the signal and N is the number of the sampled points in the acquired signal (in this study, N=500, which means the first 100 μs of the waveform will be taken into account). FIG. 6C presents that the energy of the first 100 μs waveform which changes with the various degree of osseointegration of the bone tissue under the interrogator of the fundamental longitudinal guided wave. The numerical results establish a clear trend that the amplitude and the energy of L(0,1) wave in the prosthesis rod decreases with the degree of bone tissue osseointegration. Both the waveforms and the decreasing energy trend will be validated by experimental testing in the laboratory in the next section.

As described herein, the titanium rod with PZT elements bonded is implanted in an actual sawbone to mimic the osseointegrated prosthesis in an adult femur in the laboratory. A National Instruments (NI) 8101 chassis with PXIe-6124 and PXIe-6361 data acquisition cards (DACs) installed is employed to be the target controller to execute the wave generation and wave sensing process. Two DACs offer 4 output channels and 4 input channels for the actuators and sensors, respectively, with a maximum sampling frequency 1 MHz. The entire data acquisition process was driven by a user interface coded in LabVIEW.

A PC with LabVIEW is utilized to be the master controller carrying out all the commands, transferring and saving experimental data, analyzing the waveform response and evaluating the performance of the prosthesis. All captured waveforms are transferred from the NI chassis to the remote PC in real-time. Another user-friendly interface is created to run under LabVIEW to visualize and analyze changes in the wave energy correlated to both the degree of integration and the looseness of the prosthesis in the bone.

For the experimental validation of osseointegration in a femur bone, a 30-minute epoxy with a fully cured density of 1550 kg/m$^3$ and elastic modulus of 3.5 GPa was applied to the bone-prosthesis interface to mimic the post-operative healing process by offering increasing elastic modulus and density. Repeated L(0,1) mode guided waves are generated and converted to a scalar metric through the signal energy using equation (16). While the cured density is nearly identical to the sawbone density, the epoxy modulus is slightly greater than half that of bone but in this case the epoxy curing is only intended to show sensitivity. Clearly, had the epoxy cured to have a modulus closer to that of bone, the change in acoustic impedance would be even more dramatic making the change in signal energy even more pronounced.

After defining the rod geometry and locations of the PZT elements in ABAQUS, the density, elastic modulus, and the Poisson's ratio of the titanium rod and the femur sawbone (which are the most important acoustic medium parameters) are selected as the parameters to update in the model. Model updating is performed to achieve a good fit between the experimental and simulation waveforms. The density and elastic modulus describe the absolute value of acoustic impedance of the bone and rod, which result in the change of wave amplitude.

Figure 7A:
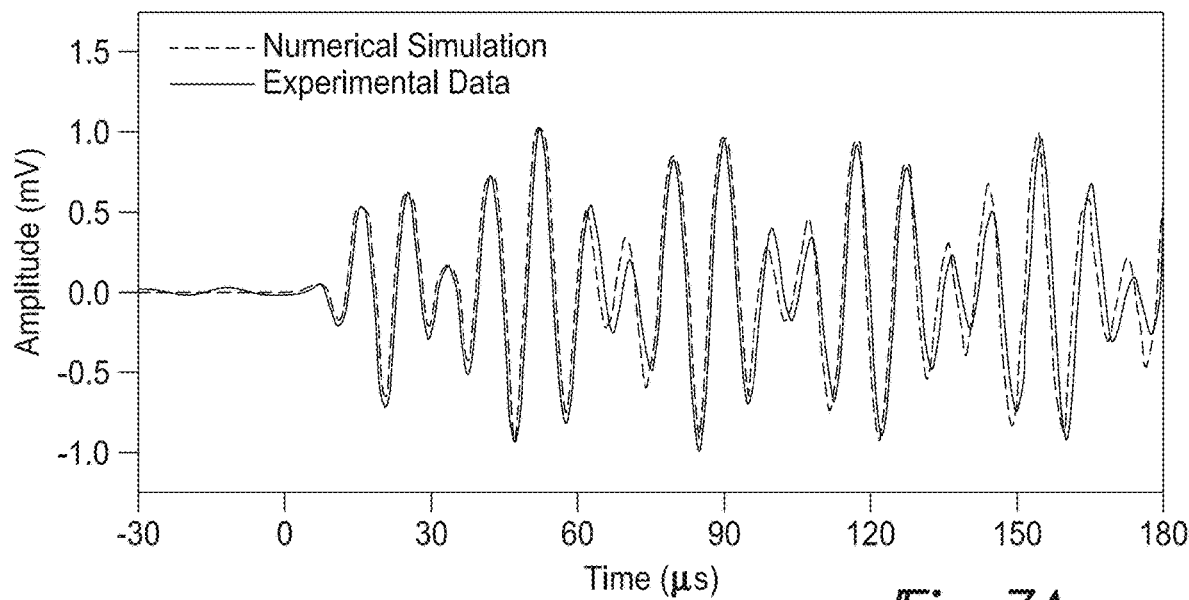
FIG. 7A shows before osseointegration (0%).

Additionally, the elastic modulus and the Poisson's ratio are adjusted to reconcile the waveform with physical measurements including crest, trough, and phase. It is noted that all the material properties shown in the previous section (Table 1) are updated values based on the experimental results. It is noted that, the signal amplitude or energy is a continuous function of the density and elastic modulus of the bone tissue. Thus, the comparisons of the numerical and experimental results for 0% and 100% degree of osseointegration are enough for model updating. After the FE model updating, the waveform captured by the sensor before the osseointegration experiment has a good agreement with the 0% degree of osseointegration simulated by ABAQUS as demonstrated in FIG. 7A. Meanwhile, the simulated waveform with 100% osseointegration of the bone tissue is nicely fitted into the measurement when the epoxy is fully solidified after 30 minutes (FIG. 7B).

Gaussian processes regression (GPR) is used to analyze the relationship between the energy of the longitudinal wave mode and the degree of osseointegration. The purpose of GPR is to model a relationship between wave energy and osseointegration based on the experimental results. Two tests were carried out with a GPR model fit to each experimental result as shown in FIGS. 8A and B. The energy of the received wave decreases with the osseointegration in the first 30 minutes. After the epoxy solidifies, the energy reached a stable stage representing the healthy state of the osseointegrated prosthesis. The general standard deviation values in the experiments range from 1.76 to 1.79% of the normalized energy. It also worth mentioning that the two GPR models are very similar underscoring the repeatability of the approach.

Figure 9:
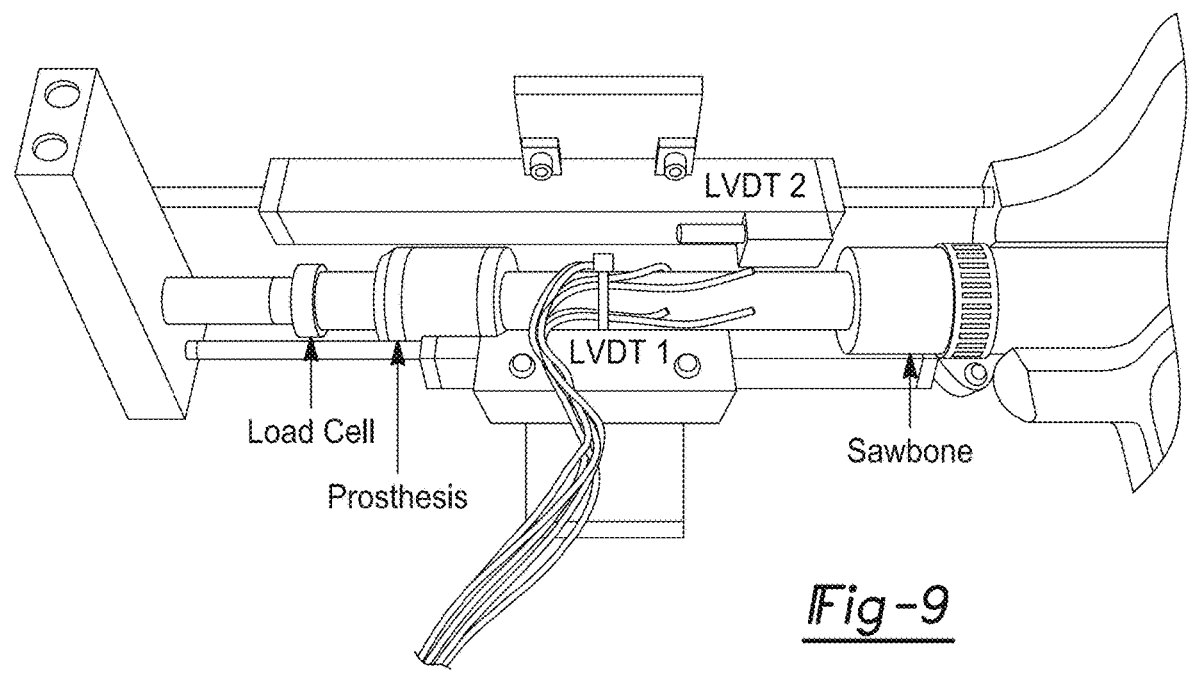
FIG. 9 is an experimental set-up with two LVDTs and one load cell.

Next, considering the fact that 5 to 7% of implants have to be removed because of loosening of the prosthesis, fixture loosening and pullout is experimentally modeled for long-term monitoring research. FIG. 9 shows the experimental set-up of penetration depth (i.e., pullout) testing. The femur sawbone is clamped on a rigid structure. Clay is employed to simulate the interfacial tissue between the prosthesis and the bone. The prosthesis fixture is slowly pulled of the bone using an actuator. Towards this end, the prosthetic titanium rod is connected to a horizontal turn screw motor (FIG. 9). The motor is loaded in a quasi-static fashion with increasing displacement controlled by LabVIEW. Two linear variable displacement transducers (LVDTs) and one load cell were employed to monitor both the displacement and force of the pullout maneuver.

Figure 10A:
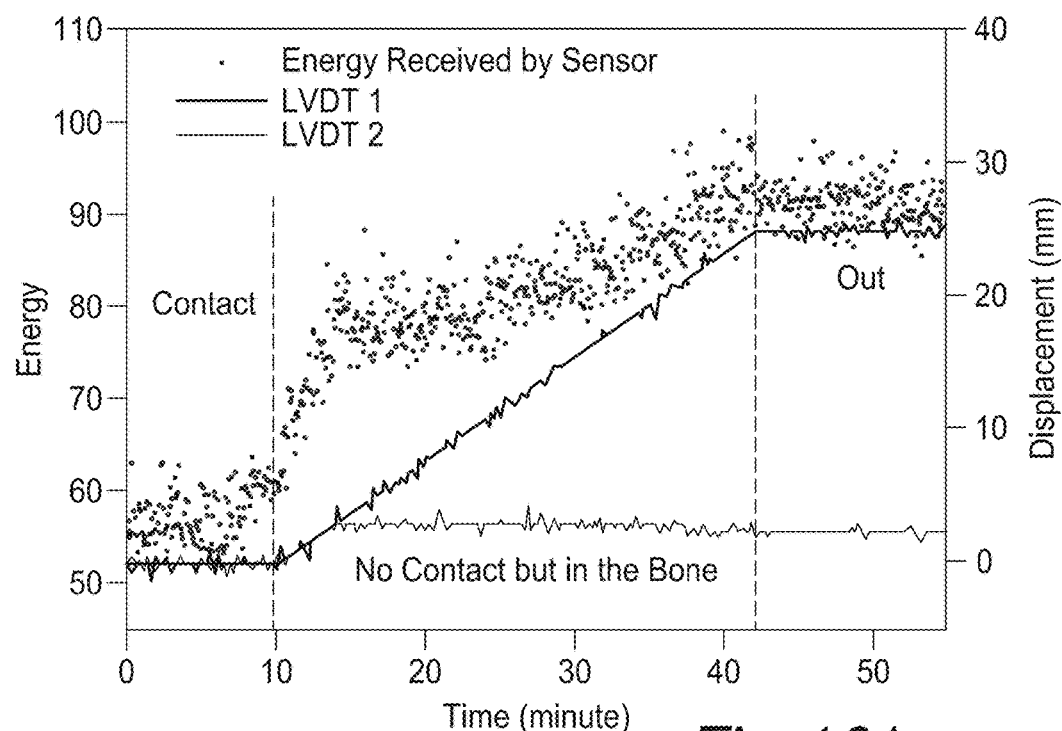
FIG. 10A is sample 1 of pull-out experimental results.
Figure 10B:
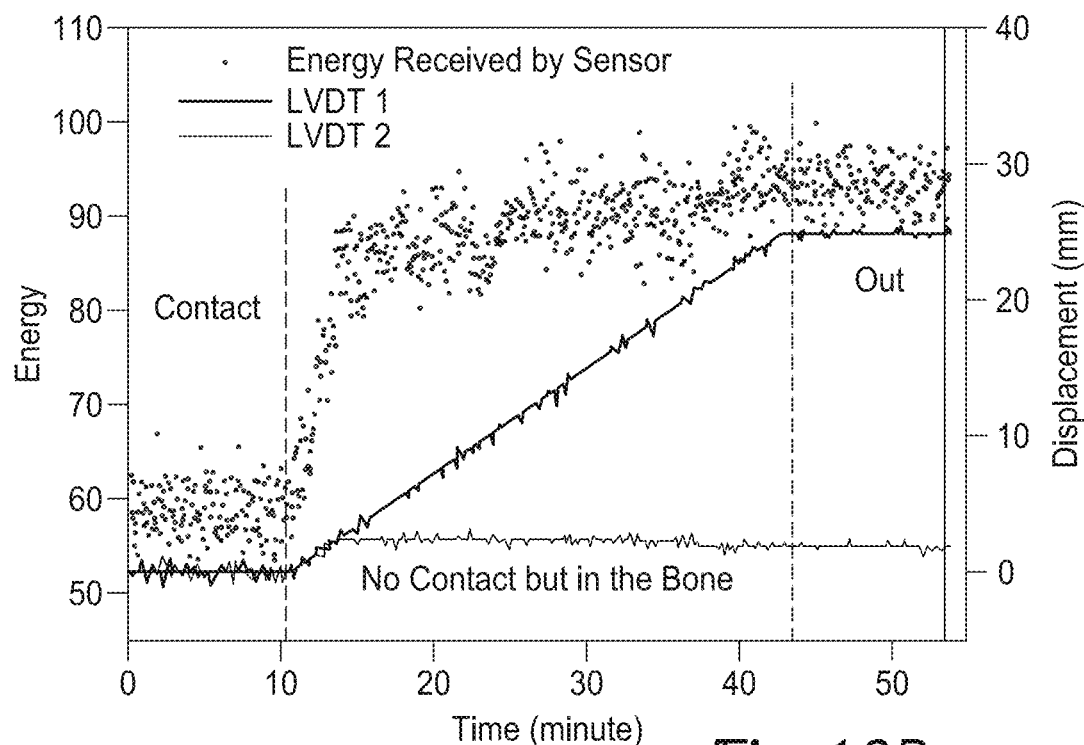
FIG. 10B is sample 2 of pull-out experimental results.
Figure 10C:
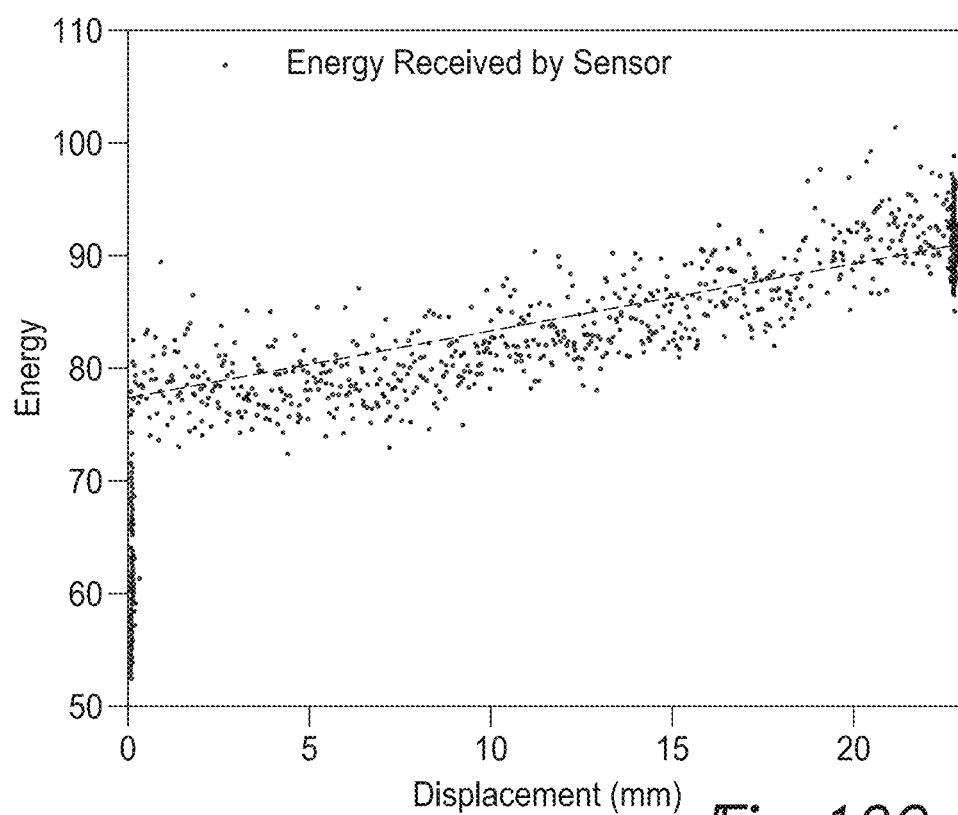
FIG. 10C is sample 1 stage 2 of pull-out experimental results.

FIG. 10 shows the energy of the longitudinal guided waves received by the sensor array as a function of the pull-out displacement. Two stages are observed. First the pullout force begins to relax the pressure of the rod on the bone at the flat circular surface of the rod. This stage continues until the pressure on the bone at this surface vanishes. Next is the second stage where the rod is now moving out of the bone effectively sliding along the bone's inner cavity. Two LVDTs are used to measure the displacement of the rod to the actuator and the bone relative to the actuator. To ease the readability of the experimental results, the energy is demonstrated in two separated ranges. In the first stage, the wave energy significantly increases at the beginning of the separation of the rod and bone, thereby relaxing pressure on the contact surface of the rod inside the bone. After the initial detachment, the energy slowly increases due to the pullout, which changes with the penetration depth. FIG. 10A plots energy (along with displacements) for sample 1 and FIG. 10B plots it for sample 2. FIGS. 10C-10D show the same results just plotting stage 2. The software used to run the experiment can identify both the penetration depth and the contact status by the interrogation of the fundamental longitudinal guided wave.

According to the principles of the present teachings, guided waves (e.g. longitudinal, torsional, flexural, or any other wave) are provided as a tool to predict the degree of osseointegration of bone-prosthesis implants after surgery for clinical decision making (e.g., when can an osseointegrated prosthesis be loaded?). In some embodiments, this active sensing strategy is conducted from outside the limb on the percutaneous extension of the prostheses and utilizes piezoelectric wafers to introduce guided wave into the prosthesis fixture. Reflected guided waves are employed to assess the degree of osseointegration and loosening of the prosthesis based on a scalar energy matric. The functionality of the guided wave sensing strategy is validated in the laboratory on models consisting of titanium femoral stems implanted in synthetic sawbones. Fundamental longitudinal waves are introduced into the prosthesis rod to interrogate the prosthesis-bone interface. An important contribution of the study is the theory of tuning guided waves in solid cylindrical rods with ideal bonding of a PZT wafer. The optimization of the length of the PZT and the excitation frequency are achieved based on the tuning curve of longitudinal waves to enhance the accuracy of the present technique.

The sensing strategy is also numerically simulated to estimate the degree of osseointegration after surgical placement. 3D laser scanning is utilized to provide a precise digital mapping of the femur sawbone geometry for a numerical model in ABAQUS. Osseointegration is mimicked by increasing the elastic modulus and density of the bone tissue at the prosthesis surface. The energy of received guided waves decreases with the healing processing as is validated by the numerical model. Full osseointegration results in approximately a 50% change in longitudinal wave energy. To verify the sensitivity of the longitudinal wave model on changes in an interface between the prosthesis and bone, experimental results were conducted with epoxy serving as a surrogate for bone healing. Again, results confirmed energy of the wave mode sensitive to changes in the interface. In addition, the separation of the prosthesis from the bone was also studied via pull-out experiments whose results show the wave energy has a significant increase with the pullout. Hence, the strategy of the present teachings is sensitive and selective to both osseointegration and prosthesis loosening. These results demonstrate the great potential of guided waves for clinical evaluation of the bone-prosthesis interface.

In accordance with the teachings herein, in some embodiments determination and detection of cracks or fracture within a bone can be achieved. For discussion and validation and to mimic bone fracture, a longitudinal crack is introduced in the bone starting at the bone end where the prosthesis is inserted. The size of the longitudinal crack is 25.4 mm long and 0.2 mm thick, which is a through-all cut crack near sensor 1 whose surface is parallel to the sensor 1-3 plane (a plane parallel to the y-axis in FIG. 11B). The final bone fracture model is shown in FIG. 11B.

To obtain accurate displacement waveforms, implicit ABAQUS/standard is used with simulations performed over a 200 µs computational time period. The strain field of the whole model, the displacement of the titanium rod, and the electrical potentials on the top surfaces of the four PZT sensors are output from ABAQUS and analyzed.

Figure 12A:
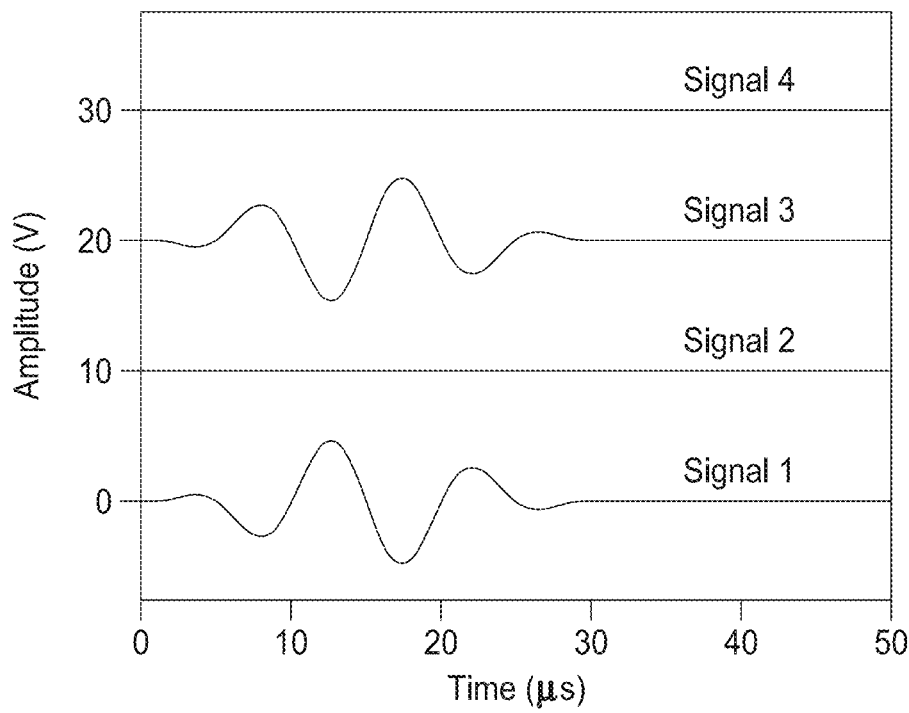
FIG. 12A shows excitation signals for F(1,1) mode of guided wave for 1-3 direction.
Figure 12B:
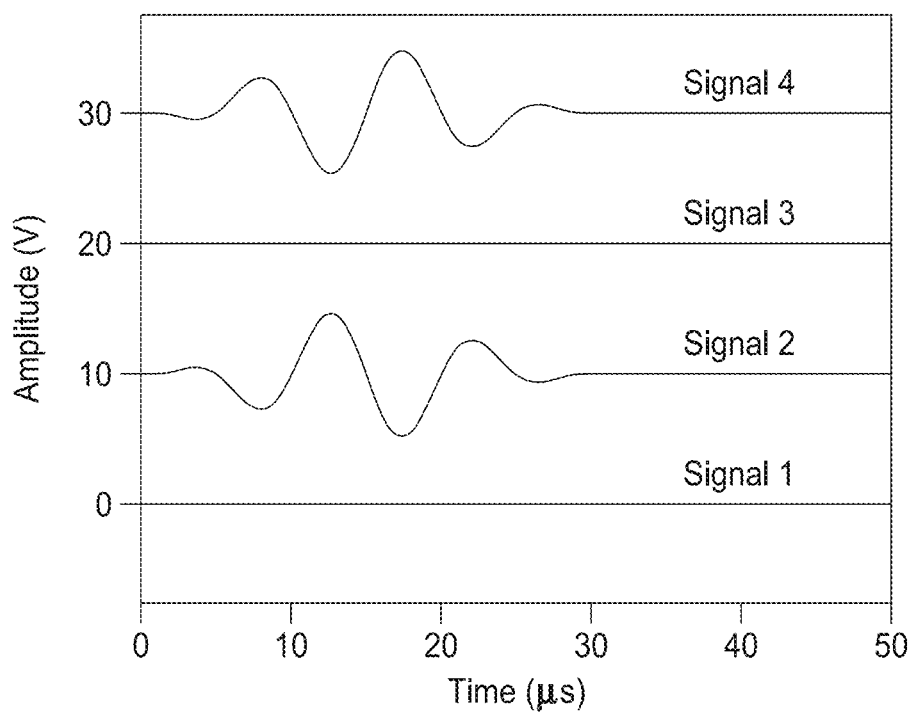
FIG. 12B shows excitation signals for F(1,1) for 2-4 direction.

The titanium rod with the PZT wafer arrays at two circumference locations is implanted in the synthetic sawbone to mimic the osseointegrated prosthesis in the femur bone. A three-cycle Hanning window tone-burst signal is then employed as the excitation signal for the PZT actuator elements, whose formula is given at Equation 10. However, it should be understood that the principles of the present teachings are not limited to the particular waveform described (Equation 10), but are equally applicable to any other waveform that is either finite in duration or infinite. Two F(1, 1) modes can be introduced based on the PZT elements bonded to the rod circumference. To introduce a directional flexural guided wave, two PZT elements on opposite sides of the rod diameter are excited with the same excitation signals but perfectly 180° out-of-phase. This approach ensures two different F(1, 1) mode can be introduced into the prosthesis rod: one is launched by the actuator pair 1 and 3 which propagates along 1 and 3 direction, and the other is launched by actuator 2 and 4 propagating along 2 and 4 direction (see FIG. 11B). However, it should be understood that in some embodiments a single PZT element can be used to introduce a flexural wave. The excitation signal which consist of a three period 100 kHz signal generating different guided waves are represented in FIGS. 12A and 12B at the four PZT elements.

Figure 13A:
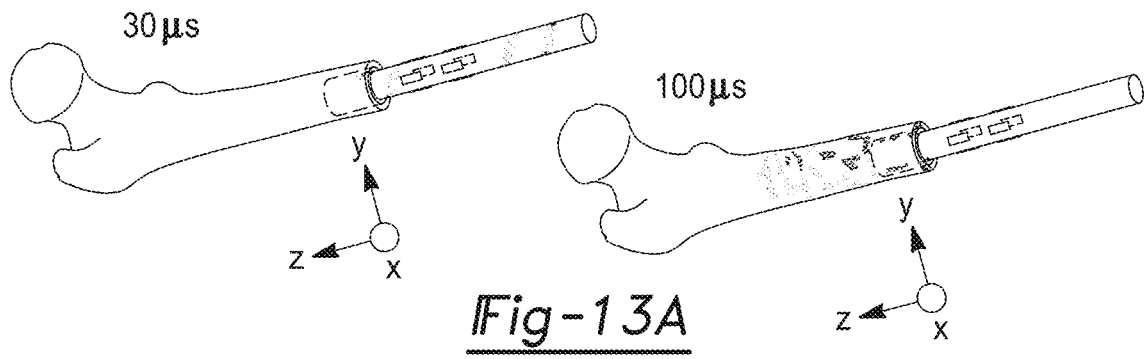
FIG. 13A shows visualization results of the healthy bone-prosthesis model excited by actuator 1 and 3.
Figure 13B:
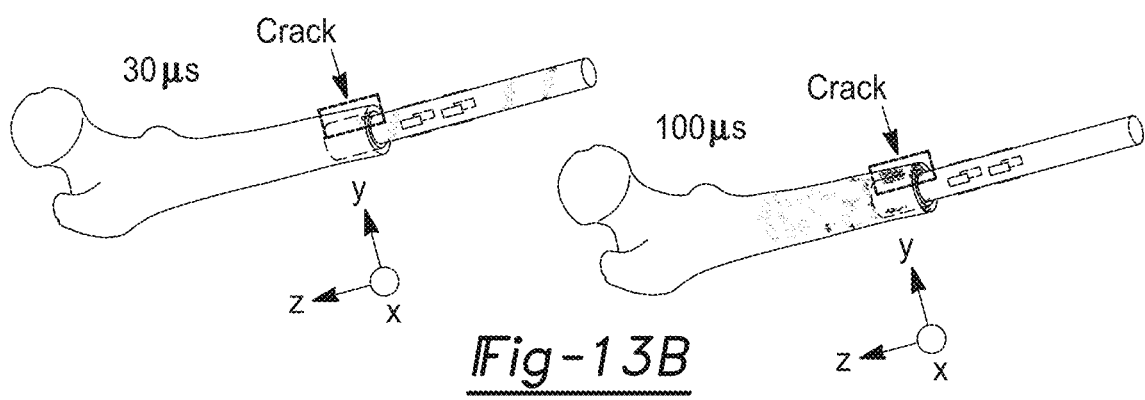
FIG. 13B shows visualization results of the bone-prosthesis model with a longitudinal crack in bone excited by actuator 1 and 3.
Figure 13C:
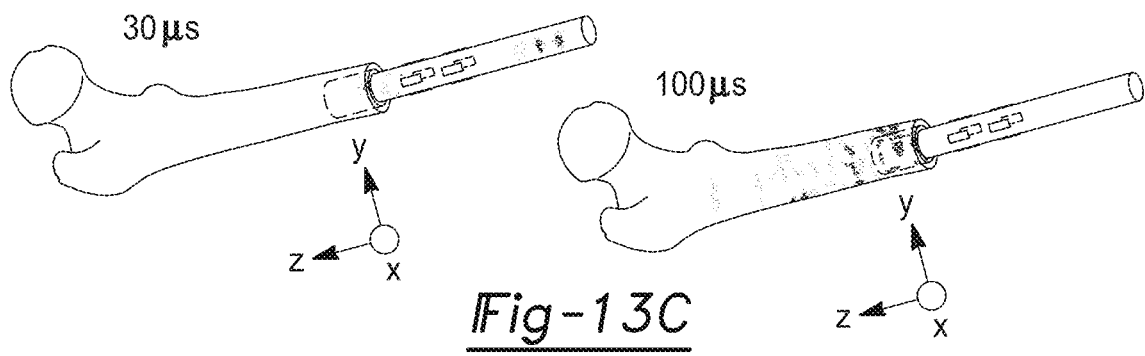
FIG. 13C shows visualization results of the healthy bone-prosthesis model excited by actuator 2 and 4.
Figure 14A:
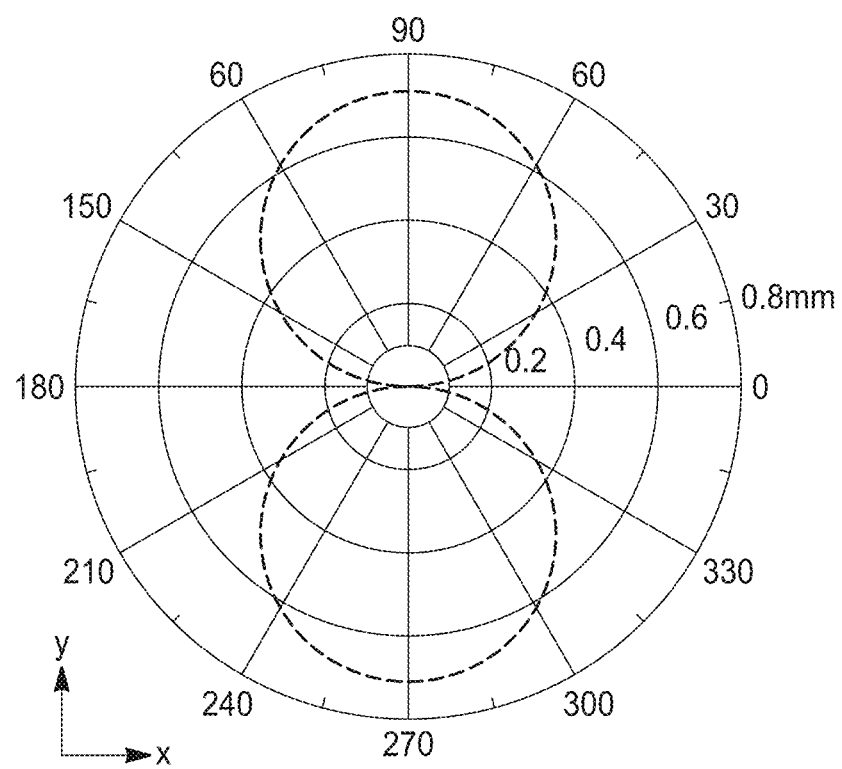
FIG. 14A is a peak circumferential displacement excited by actuator pair 1 and 3.
Figure 14B:
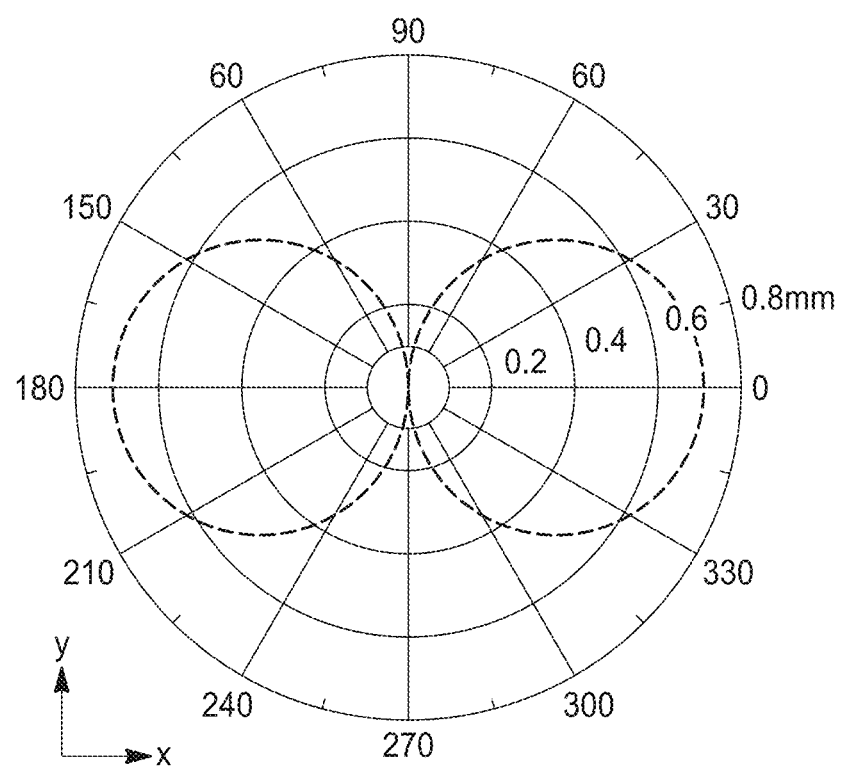
FIG. 14B is a peak circumferential displacement excited by actuator 2 and 4.

FIGS. 13A and 13C show snapshots of the 1-3 direction and 2-4 direction flexural guided wave propagation in the pristine (i.e., no fracture is present) bone-prosthetic model in ABAQUS at t=30 µs and t=100 µs, respectively. FIGS. 14A and 14B plot the circumferential peak displacement on the prosthetic titanium rod circumference under the excitation signal represented in FIGS. 13A and 13C, respectively, which are flexural modes in two orthogonal planes of propagation. The plots of circumferential peak displacement clearly confirm that the flexural wave mode dominates in the plane defined by the actuator pair used to launch the wave. It is this insight that allows the circumferential location of the crack to be identified.

Figure 13D:
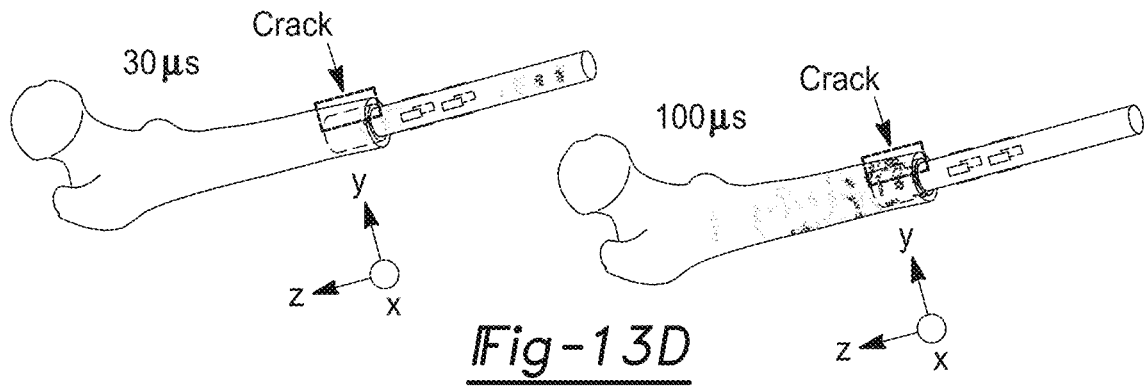
FIG. 13D shows visualization results of the bone-prosthesis model with a longitudinal crack in bone excited by actuator 2 and 4.

For the bone fracture model, FIG. 13B and FIG. 13D demonstrate the strain field results of the flexural wave when the bone has a fracture will scatter from the fractured bone surfaces in FE model at the time 30 µs and 100 µs, respectively. The strain field changes (due to stress concentrations at the crack) due to the bone fracture. In addition, the guided wave is continuously reflected and scattered by the fracture plane which could be regarded as a new wave source when considering the measured waves reflected back to the sensing circumferential array.

Figure 15A:
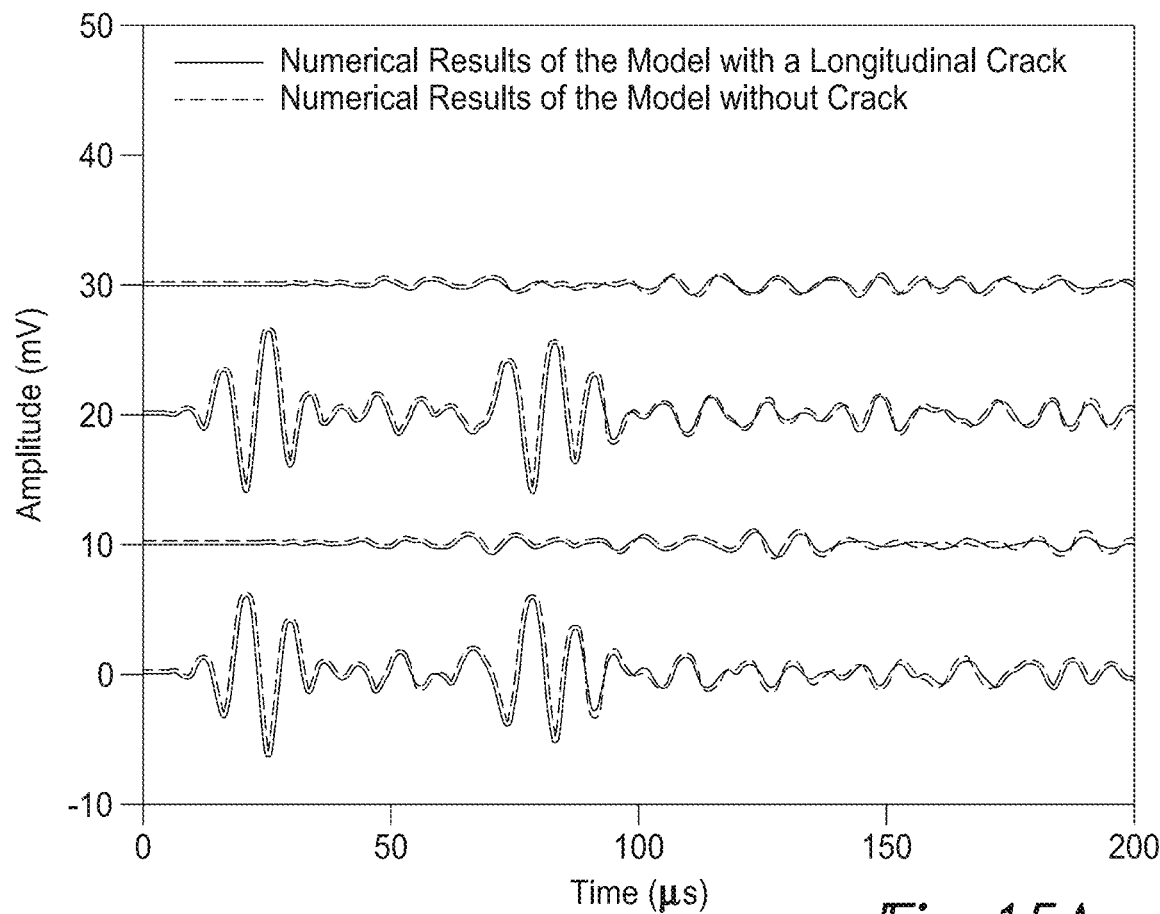
FIG. 15A shows waveforms of all four PZT sensors.

The waveforms captured by the sensing PZTs in the numerical model are shown in FIG. 15A. The gray solid lines are the waveforms of the bone-prosthesis model without bone fracture while the red lines are the received signals with the longitudinal fracture crack FIG. 15A. In addition, the waveforms acquired by PZT element 1 is plotted separately to show the difference between the waveform of the bone with fracture compared to the pristine bone case in FIG. 15B.

It should be noted that the waveform amplitude of the fractured bone case is cyclically higher and lower than the waveform from the pristine case. This is clear evidence that a new wave packet is involved and is originating from the fracture surfaces. Based on Huygens' principle, the fracture crack could be regarded as a new wave source producing wave packets after flexural guided waves propagating along the rod exciting the crack. Hence, viewing the differences in the two signals (case of the unknown bone condition and the healthy baseline) in the time domain is an obvious approach to identifying the bone fracture. In order to extract the bone fracture signal features, a time-frequency domain representation of the difference signal is used to identify and characterize the new wave packets. The Gabor wavelet transform (WT) is performed on the time domain difference signal to obtain the time-frequency spectrogram. However it is well understood other time-frequency transform methods could be used including wavelets with different kernel functions, the Hilbert-Huang Transform, among many others.

Figure 15B:
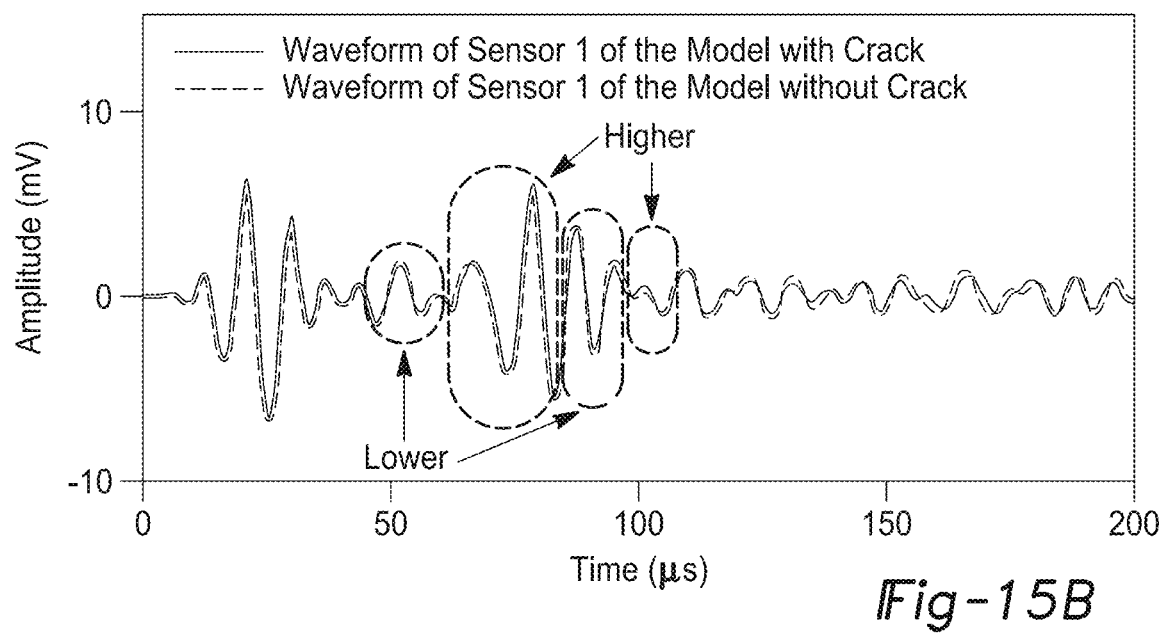
FIG. 15B shows waveform of PZT sensor 1.

In each time-frequency representation of the difference signal in FIG. 15B, a top plot is the difference signal in time domain and the left plot is the Fourier spectrogram shown in the frequency domain. The right bottom contour mapping is the WT feature in time-frequency domain. A 0.25 mV threshold is set to indicate the arriving time of the first wave package of the difference signal which is plotted as a straight line.

Figure 16A:
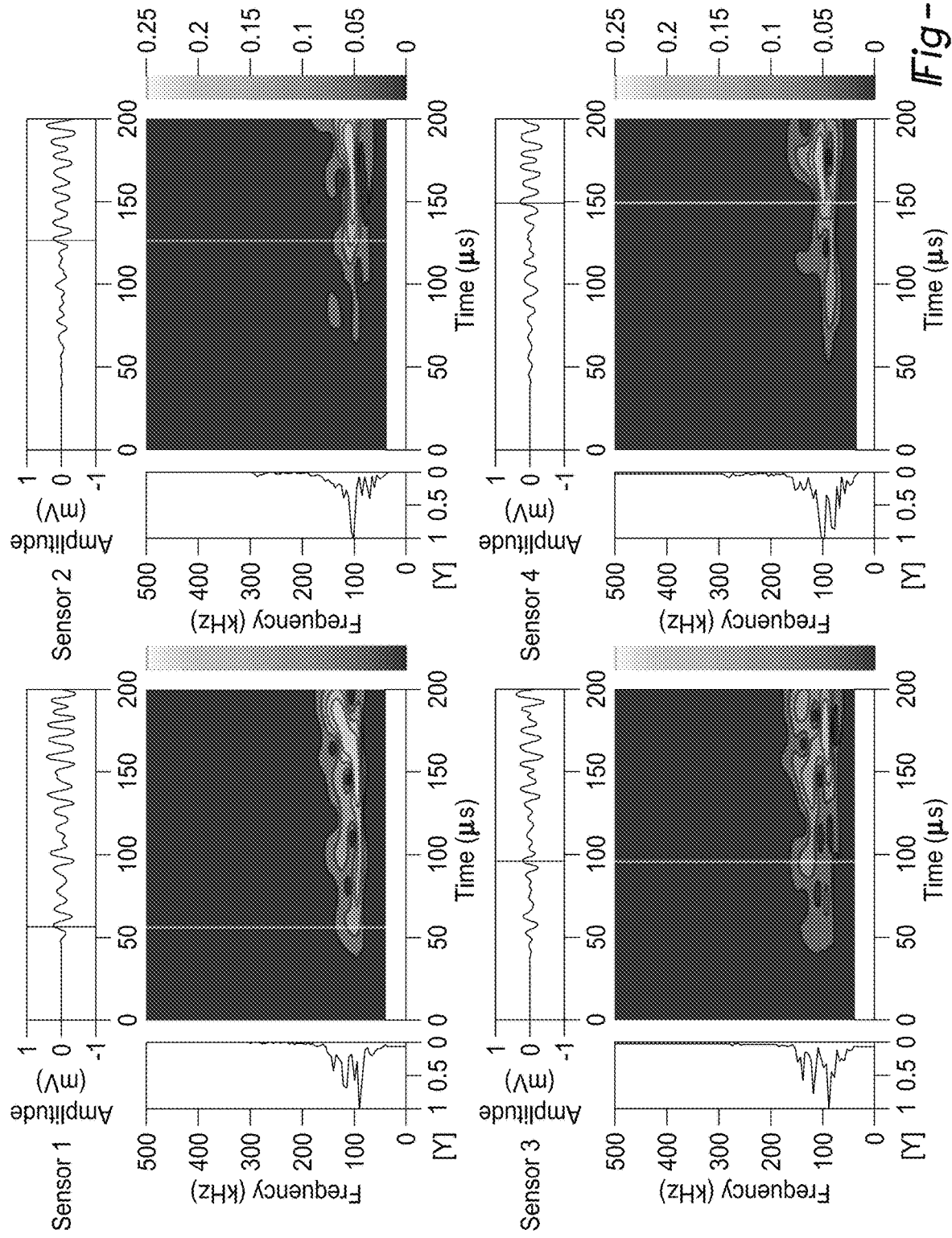
FIG. 16A shows 1-3 direction flexural mode of time-frequency representations of all the difference signals under different excitation.
Figure 16B:
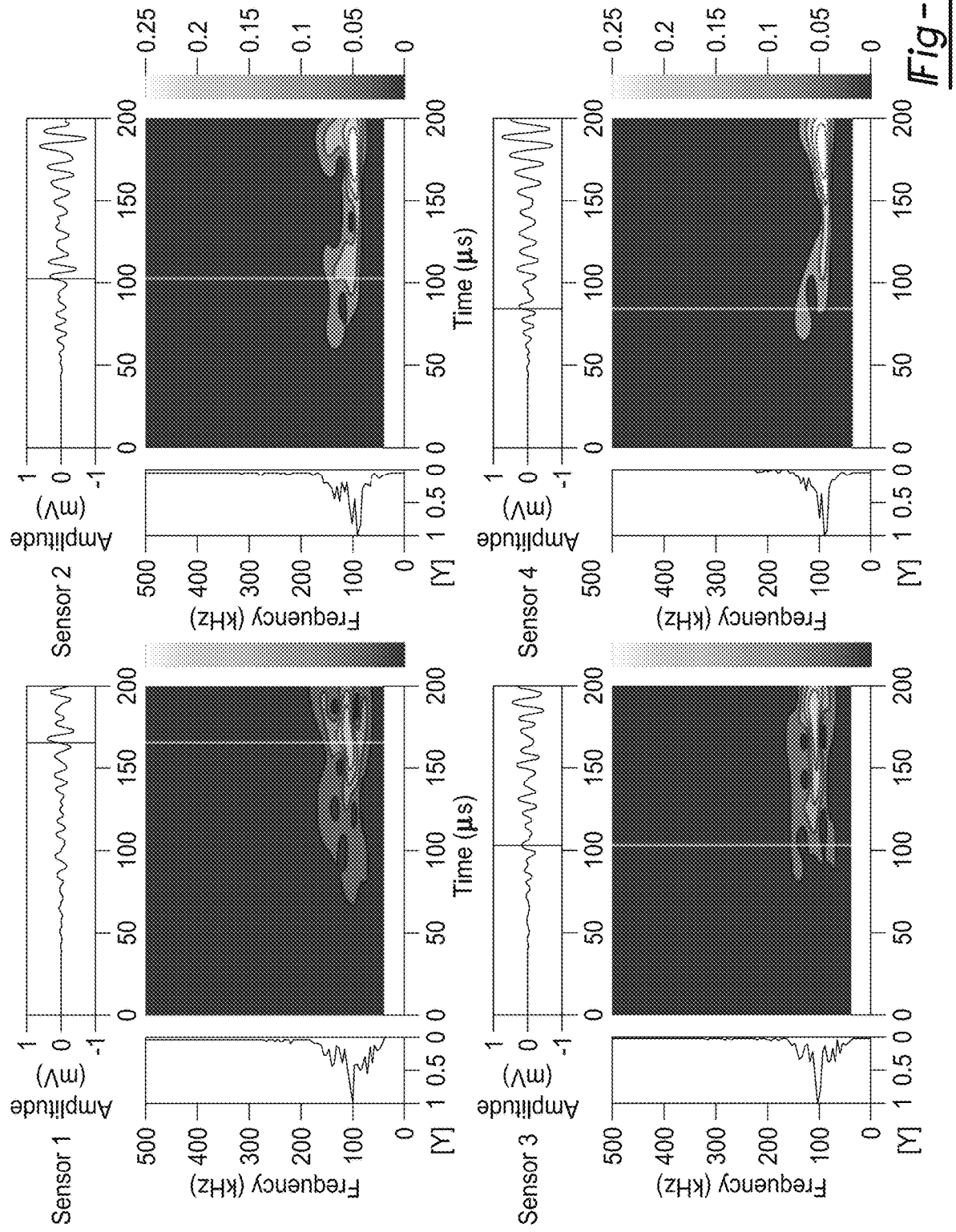
FIG. 16B shows 2-4 direction flexural mode of time-frequency representations of all the difference signals under different excitation.

For the 1-3 direction excitation, the arrival time of the new wave packet to the four PZT sensors are 56.8 µs, 126.0 µs, 95.8 µs, and 148.8 µs, respectively (as shown in FIG. 16A). For the 2-4 direction flexural wave, the arrival time of the wave to the four PZT sensors are 165.2 µs, 102.8 µs, 102.8 µs, and 84.6 µs, respectively (as shown in FIG. 16B). Considering the difference signal was caused by an excitation of the crack, the arrival times obtained by different flexural guided waves are related to both the location of the bone fracture and the excitation signal. The smallest arrival time reveals the crack location, which is the bone-prosthesis interface near to sensor 1. In addition, the amplitude of the first wave package is higher when the prosthetic rod is excited by 1-3 direction flexural mode, which verifies the location of the crack should be near sensor 1 as well. It is noted that the energy of the difference signal excited by 2-4 direction flexural mode is higher than the energy excited by 1-3 direction wave after about 75 µs. That is likely due to the fact that the crack direction is parallel to the 1-3 plane, which reflects more energy to the prosthetic rod when the wave begins to propagate in the bone.

According to the present teachings, a guided wave strategy is provided to quantitatively identify the existence of fractures in a bone in which an osseointegrated prosthesis has been implanted. Fracture can occur in the bone due to overloading of the prosthesis including excessive moments applied to the percutaneous end of the prosthesis. Currently, X-rays is the only method available to identify such fractures. The SHM-based approach illustrated in this study is based on the controlled generation of guided waves in the prosthesis fixture at the percutaneous end using an array of piezoelectric wafers installed on the prosthesis structural surface. The approach is low-cost and repeatable leading to growing interest from both prosthesis manufacturers and members of the orthopedic surgical community currently performing osseointegration of prostheses. The study launches flexural waves in the titanium prosthesis with a center frequency of 100 kHz. These waves are shown to be sensitive to the existence of fracture with new wave packets generated by the fracture plane. Wavelet analysis of the new wave packets provides a convenient approach to visualization of the new wave packets generated by the fracture event leading to crack localization.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A monitoring system for an osseointegrated prosthesis comprising:
    an array of a plurality of wave-generating elements mounted to a surface of a circumferential outer side of the osseointegrated prosthesis which is configured to be percutaneous, the plurality of wave-generating elements configured to generate guided waves along the osseointegrated prosthesis interrogating an interface between bone and the osseointegrated prosthesis and resulting in a return energy waveform indicative of an osseointeration state;
    and a sensing system configured to sense the return energy waveform to determine a condition of the interface between bone and the osseointegrated prosthesis.

2. The monitoring system according to claim 1 wherein the sensing system is configured to sense an increased energy absorption condition of the interface between the bone and the osseointegrated prosthesis as the bone grows into a porous surface of the osseointegrated prosthesis.

3. The monitoring system according to claim 1 wherein the plurality of wave-generating elements are configured to generate longitudinal guided waves interrogating an interface between bone and the osseointegrated prosthesis.

4. The monitoring system according to claim 1 wherein the plurality of wave-generating elements is configured to generate torsional guided waves interrogating an interface between bone and the prosthesis.

5. The monitoring system according to claim 1 wherein the plurality of wave-generating elements is configured to generate flexural guided waves interrogating an interface between bone and the prosthesis, a first of the plurality of wave-generating elements being configured to generate a first signal and a second of the plurality of wave-generating elements being configured to generate a second signal, the first signal being 180 degrees out of phase with the second signal.

6. The monitoring system according to claim 1 wherein the plurality of wave-generating elements comprise one or more piezoelectric elements.

7. The monitoring system according to claim 1 wherein the plurality of wave-generating elements configured to generate guided waves along the osseointegrated prosthesis comprises the plurality of wave-generating elements being tuned to maximize the amplitude of strain fields associated with the guided waves.

8. The monitoring system according to claim 7 wherein the plurality of wave-generating elements is tuned based on a central frequency of an excitation signal that induces wavelengths of the guided waves and a length of each of the plurality of wave-generating elements.

9. An osseointegrated prosthesis system comprising:
an osseointegrated prosthesis member engageable with a bone along an interface;
a monitoring system operably coupled to the osseointegrated prosthesis member configured to quantitatively assess the osseointegration of the osseointegrated prosthesis member;
an array of a plurality of piezoelectric elements mounted directly to a surface of a circumferential outer side of the osseointegrated prosthesis member which is configured to be percutaneous, the plurality of piezoelectric element configured to output guided waves along the osseointegrated prosthesis member interrogating the interface between the bone and the osseointegrated prosthesis member and resulting in a return energy waveform indicative of an osseointegration state;
and a sensing system configured to sense the return energy waveform to determine a condition of the interface between bone and the osseointegrated prosthesis member.

10. The osseointegrated prosthesis system according to claim 9 wherein the sensing system is configured to sense an increased energy absorption condition of the interface between the bone and the osseointegrated prosthesis member as the bone grows into a porous surface of the osseointegrated prosthesis member.

11. The osseointegrated prosthesis system according to claim 9 wherein the plurality of piezoelectric elements are configured to generate longitudinal guided waves interrogating an interface between bone and the osseointegrated prosthesis member.

12. The osseointegrated prosthesis system according to claim 9 wherein the plurality of piezoelectric elements are configured to generate torsional guided waves interrogating an interface between bone and the prosthesis.

13. The osseointegrated prosthesis system according to claim 9 wherein the plurality of piezoelectric elements are configured to generate flexural guided waves interrogating an interface between bone and the prosthesis.

14. The osseointegrated prosthesis system according to claim 9 wherein the plurality of piezoelectric elements configured to output guided waves along the osseointegrated prosthesis member comprises the plurality of piezoelectric elements being tuned to maximize the amplitude of strain fields associated with the guided waves.

15. The osseointegrated prosthesis system according to claim 14 wherein the plurality of piezoelectric elements is tuned based on a central frequency of an excitation signal that induces wavelengths of the guided waves and a length of each of the plurality of piezoelectric elements.

* * * * *

UNITED STATES PATENT AND TRADEMARK OFFICE
CERTIFICATE OF CORRECTION

PATENT NO. : 11,678,842 B2
APPLICATION NO. : 16/642122
DATED : June 20, 2023
INVENTOR(S) : Jerome P. Lynch et al.

It is certified that error appears in the above-identified patent and that said Letters Patent is hereby corrected as shown below:

In the Claims

At Column 18, Claim number 1, Line number 48, after "state;" insert -- and --.

At Column 18, Claim number 1, Line number 49, before "a sensing" delete "and".

At Column 19, Claim number 9, Line number 36, after "state;" insert -- and --.

At Column 20, Claim number 9, Line number 1, before "a sensing" delete "and".

Signed and Sealed this
Eighth Day of August, 2023

Katherine Kelly Vidal
*Director of the United States Patent and Trademark Office*